(12) United States Patent
Yoshihara

(10) Patent No.: US 10,641,706 B2
(45) Date of Patent: May 5, 2020

(54) CELL MORPHOLOGY IMAGE PROCESSING AND CORRECTIONS

(71) Applicant: Konica Minolta, Inc., Tokyo (JP)

(72) Inventor: Yuka Yoshihara, Hino (JP)

(73) Assignee: Konica Minolta, Inc., Tokyo (JP)

( * ) Notice: Subject to any disclaimer, the term of this patent is extended or adjusted under 35 U.S.C. 154(b) by 210 days.

(21) Appl. No.: 15/736,382

(22) PCT Filed: May 24, 2016

(86) PCT No.: PCT/JP2016/065232
§ 371 (c)(1),
(2) Date: Dec. 14, 2017

(87) PCT Pub. No.: WO2016/203907
PCT Pub. Date: Dec. 22, 2016

(65) Prior Publication Data
US 2018/0188177 A1 Jul. 5, 2018

(30) Foreign Application Priority Data
Jun. 16, 2015 (JP) .................................. 2015-120726

(51) Int. Cl.
*G06K 9/00* (2006.01)
*G01N 21/64* (2006.01)
(Continued)

(52) U.S. Cl.
CPC ......... *G01N 21/6458* (2013.01); *G01N 21/64* (2013.01); *G01N 21/6428* (2013.01);
(Continued)

(58) Field of Classification Search
None
See application file for complete search history.

(56) References Cited

U.S. PATENT DOCUMENTS

| 4,326,008 A | 4/1982 | Rembaum |
| 5,326,692 A | 7/1994 | Brinkley et al. |

(Continued)

FOREIGN PATENT DOCUMENTS

| EP | 2833123 A1 | 2/2015 |
| JP | S62-267875 A | 11/1987 |

(Continued)

OTHER PUBLICATIONS

Siadat-Pajouh et al.; "Detection of Human Papillomavirus Type 16/18 DNA in Cervicovaginal Cells by Fluorescence Based in Situ Hybridization and Automated Image Cytometry"; Cytometry; vol. 15 No. 3; 1994; p. 245-257.

(Continued)

*Primary Examiner* — Atiba O Fitzpatrick
(74) *Attorney, Agent, or Firm* — BakerHostetler

(57) ABSTRACT

Provided is a technology in which an image accurately representing a distribution of an area where a specific portion of a cell in an image capturing a cell morphology is captured can be stably acquired. In order to provide the technology, an acquisition unit acquires a virtual cell distribution image in which a distribution of an assumed cell area to be assumed that a specific portion of a cell in a cell morphology image capturing a cell morphology is represented by a plurality of cell display elements, and one or more cell display elements of the plurality of cell display elements is depicted according to an operation of a user. An arithmetic unit obtains a characteristic value relevant to characteristics in appearance and characteristics in appearance of corresponding one or more assumed cell areas in the cell morphology image, with respect to each of the one or more cell display elements described above. A correction unit corrects the virtual cell distribution image to generate a cell distribution image by setting a cell display element of (Continued)

which the characteristic value is at least out of an allowable value range or within a prohibition value range to be in a state of being deleted from the virtual cell distribution image or being unadopted, in one or more cell display elements.

9 Claims, 13 Drawing Sheets

(51) Int. Cl.
*G01N 33/48* (2006.01)
*G06T 7/00* (2017.01)
*G06T 7/11* (2017.01)
*G01N 33/50* (2006.01)
*G01N 33/58* (2006.01)

(52) U.S. Cl.
CPC ......... *G01N 33/48* (2013.01); *G01N 33/5005* (2013.01); *G01N 33/582* (2013.01); *G06T 7/0012* (2013.01); *G06T 7/11* (2017.01); *G01N 2021/6439* (2013.01); *G06T 2207/10056* (2013.01); *G06T 2207/10064* (2013.01); *G06T 2207/30024* (2013.01)

(56) References Cited

U.S. PATENT DOCUMENTS

| | | | |
|---|---|---|---|
| 9,779,500 B2 | 10/2017 | Watanabe et al. | |
| 2009/0116724 A1* | 5/2009 | Yamashita | G06K 9/00127 382/133 |
| 2009/0269799 A1* | 10/2009 | Winkelman | G01N 1/2813 435/29 |
| 2010/0007727 A1* | 1/2010 | Torre-Bueno | G01N 21/6458 348/79 |
| 2015/0087240 A1* | 3/2015 | Loewke | G06T 7/0016 455/67.11 |
| 2015/0371400 A1* | 12/2015 | Farsiu | G06T 7/0012 382/128 |
| 2016/0018389 A1* | 1/2016 | Koide | C12N 5/0645 435/34 |
| 2016/0025612 A1* | 1/2016 | Kuninori | C12M 41/36 382/133 |

FOREIGN PATENT DOCUMENTS

| | | |
|---|---|---|
| JP | 2000-321031 A | 11/2000 |
| JP | 2008-188012 A | 8/2008 |
| JP | 2009-063508 A | 3/2009 |
| JP | 2011-210156 A | 10/2011 |
| JP | 2011-243188 A | 12/2011 |
| JP | 2012-037432 A | 2/2012 |
| WO | WO 2013/146843 A1 | 10/2013 |
| WO | WO 2014/140085 A1 | 9/2014 |
| WO | WO 2015/002082 A1 | 1/2015 |

OTHER PUBLICATIONS

European Patent Application No. 16811382.7; Extended Search Report; dated May 3, 2018; 10 pages.

Blaaderen et al.; "Synthesis and characterization of colloidal dispersions of fluorescent monodisperse silica spheres"; Langmuir; vol. 8(12); 1992; p. 2921-2931.

Yang et al. "Formation of two types of highly luminescent SiO2 beads impregnated with multiple CdTe QDs"; New Journal Chemistry; vol. 33; 2009; p. 561-567.

Han et al.; "Quantum-dot-tagged microbeads for multiplexed optical coding of biomolecules"; Nature and Biotechnology; vol. 19; 2001; p. 631-635.

International Patent Application No. PCT/JP2016/065232; Written Opinion and Search Report; dated Aug. 30, 2016; 14 pages.

\* cited by examiner 0.3

AREA OF ASSUMED CELL AREA
(AFTER NORMALIZATION WITH AVERAGE VALUE)

10
CHROMATICNESS OF ASSUMED CELL AREA 0.3
DEGREE OF CIRCULARITY OF ASSUMED CELL AREA

AREA OF ASSUMED CELL AREA
(AFTER NORMALIZATION WITH AVERAGE VALUE)

CELL MORPHOLOGY IMAGE PROCESSING AND CORRECTIONS

TECHNICAL FIELD

The present invention relates to an image processing device, an image processing method, and an image processing program, and in particular, relates to an image processing technology in which an image representing a distribution of an area to be assumed that a specific portion of a cell in an image capturing a cell morphology is captured, is set to a target.

BACKGROUND ART

A so-called pathological diagnosis has been actively performed in which a tissue section sampled from a biological object of human beings, animals, or the like is observed by a microscope, and the presence or absence of a pathological change, the type of pathological change, or the like is diagnosed. In such a pathological diagnosis, it is general that the tissue section, which is a diagnosis target, is subjected to treatments such as fixing, embedding, slicing, and staining in this order, and then, is provided to the observation using the microscope.

The observation using the microscope, for example, includes bright field observation, fluorescent observation, and the like, and a bright field image can be acquired by imaging in the bright field observation, and a fluorescent image can be acquired by imaging in the fluorescent observation. The bright field image, for example, includes an image capturing a plurality of cell morphologies in the tissue section stained with a predetermined staining reagent (also referred to as a cell morphology image). In addition, the fluorescent image, for example, includes an image capturing the emission of a fluorescent substance contained in particles which are bonded to a specific substance (also referred to as a light emitting state image).

Further, in the cell morphology image, an image where a distribution of an area in which a specific portion of a cell is captured (also referred to as a cell area) is represented by a display element (also referred to as a cell distribution image) can be acquired, and an image in which a distribution of the specific substance is represented by the display element (also referred to as a substance distribution image) can be acquired from the light emitting state image. Here, a case is considered in which the specific substance, for example, is a specific protein in a cancer tissue, and the specific portion is a cell nucleus.

In this case, a feature amount quantitatively representing an expression state of the specific substance in the tissue section can be calculated from the cell distribution image and the substance distribution image. For example, a feature amount such as the existing number of specific substances per one cell nucleus and the existing number of specific substances per unit area of the cell nucleus can be calculated from a relationship between a distribution of a fluorescent bright point in the substance distribution image and a distribution of a cell area in the cell distribution image. By using such a feature amount, it is possible to perform a pathological diagnosis with respect to various cancers or the like. At this time, for example, the feature amount can be used in the form of a histogram or the like in which a plurality of values are sorted into blocks as a class, and a frequency for each block is represented by a bar graph. Accordingly, a clue at the time of specifically determining a degree of malignancy or the like of the cancer of a patient can is obtained.

Here, in order to accurately perform such a pathological diagnosis, it is necessary to acquire a cell distribution image accurately reflecting an actual state of the tissue section.

Here, the light emitting state image is an image which captures a state where a fluorescent substance emits light having a specific wavelength to the dark background and has a comparatively high contrast. For this reason, for example, extraction and binarization processing of a color component according to a specific wavelength by using the light emitting state image as a target are sequentially performed, and thus, the distribution of the specific substance can be accurately detected. That is, a substance distribution image accurately reflecting the actual state of the tissue section can be comparatively easily acquired. On the other hand, the cell morphology image displays a tendency in which the contrast is obviously low, compared to the light emitting state image. For this reason, various image processings for obtaining a cell distribution image from the cell morphology image have been proposed (for example, Patent Literatures 1 and 2).

For example, in Patent Literature 1, a pixel group, which is a candidate of a cell center, is extracted from the cell morphology image, only a pixel suitable as the cell center in the pixel group is selected according to a predetermined criteria, and a pixel forming the outline of the cell is selected from positional information of the selected cell center pixel and a direction of a concentration gradient of the peripheral pixel. In addition, in Patent Literature 2, a cell group having the characteristics similar to those of a specific cell of interest which is designated by a user from a plurality of cells in the cell morphology image subjected to predetermined processing is automatically extracted.

CITATION LIST

Patent Literature

Patent Literature 1: JP 3314759 B2
Patent Literature 2: JP 4801025 B2

SUMMARY OF INVENTION

Technical Problem

However, a variation is capable of occurring in the shape, the color, the size, or the like of the specific portion in the cell morphology image, according to the state of the tissue section and a stained state. For this reason, in the technology of Patent Literature 1 described above, for example, there is a case where the tissue section provided to the pathological diagnosis is densely stained, and in such a case, it is difficult to select the pixel forming the outline of the cell by using a concentration gradient. In addition, in the technology of Patent Literature 2 described above, a plurality of cells in the cell morphology image are narrowed into a part of the cell group, and thus, the number of cells extracted from the cell morphology image decreases.

Thus, in the technology of Patent Literature 1 described above, there is a case where the cell area is not accurately extracted from the cell morphology image without any omission, according to the circumstance of the cell morphology image. In addition, the technology of Patent Literature 2 described above, is originally a technology narrowing the cell extracted from the cell morphology image, and a case easily occurs in which the cell area is not accurately extracted from the cell morphology image without any omission.

In response to such problems, for example, a method is considered in which an operator surrounds a portion to be assumed as a cell area on a cell morphology image by a line or the like, and thus, a cell distribution image is generated. In addition, for example, a method or the like is also considered in which an operator corrects an image in which a distribution of a cell area obtained by performing image processing with respect to a cell morphology image is represented by a display element, with reference to the cell morphology image.

However, when it is assumed whether or not it is the cell area capturing the specific portion of the cell on the cell morphology image, a variation is capable of occurring in the assumption according to various factors such as a difference in a degree of skill and the sense of a determination criteria between operators, and a difference in the organizations to which the operators belong. As a result thereof, a variation is capable of occurring in the cell distribution image.

Here, in order to reduce such a variation, a system (also referred to as a double check system) is considered in which a cell distribution image obtained by the correction of one operator, is corrected by the other operator, as necessary, but a decrease in an operation efficiency is capable of occurring. Furthermore, even in a case where a variation among individuals can be reduced by the double check system, it is difficult to reduce a variation due to a difference in the organizations to which the operators belong.

The present invention has been made in consideration of the problems described above, and an object of the present invention is to provide a technology in which it is possible to stably acquire a distribution of an area where a specific portion of a cell in an image capturing a cell morphology is captured is accurately represented.

Solution to Problem

In order to solve the problems described above, an image processing device according to one aspect includes a display control unit, an input unit, an acquisition unit, an arithmetic unit, and a correction unit. Here, the display control unit displays a cell morphology image capturing a cell morphology in a tissue section of a biological object stained with a staining reagent on the display unit. The input unit inputs a signal according to an operation of a user. The acquisition unit acquires a virtual cell distribution image depicting one or more cell display elements of a plurality of cell display elements, according to the signal input from the input unit in a state in which a distribution of an assumed cell area to be assumed that a specific portion of a cell in the cell morphology image is captured is represented by the plurality of cell display elements, and the cell morphology image is displayed on the display unit. The arithmetic unit obtains a characteristic value relevant to at least one type of characteristics of one type or more characteristics in appearance, and one type or more characteristics in appearance of an assumed cell area corresponding to the cell display element of the cell morphology image, with respect to each of one or more cell display elements. The correction unit corrects the virtual cell distribution image to generate a cell distribution image by setting a cell display element of which the characteristic value is at least out of an allowable value range or within a prohibition value range to be in a state of being deleted from the virtual cell distribution image or being unadopted, in one or more cell display elements.

An image processing method according to another aspect includes a step (a) to a step (c). Here, In the step (a), an acquisition unit acquires a virtual cell distribution image depicting one or more cell display elements of a plurality of cell display elements, according to a signal input according to an operation of a user in a state in which a distribution of an assumed cell area to be assumed that a specific portion of a cell in a cell morphology image capturing a cell morphology in a tissue section of a biological object stained with a staining reagent is represented by the plurality of cell display elements, and the cell morphology image is displayed on a display unit. In the step (b), an arithmetic unit obtains a characteristic value relevant to at least one type of characteristics of one type or more characteristics in appearance, and one type or more characteristics in appearance of an assumed cell area corresponding to the cell display element of the cell morphology image, with respect to each of one or more cell display elements. In the step (c), a correction unit corrects the virtual cell distribution image to generate a cell distribution image by setting a cell display element of which the characteristic value is at least out of an allowable value range or within a prohibition value range to be in a state of being deleted from the virtual cell distribution image or being unadopted, in one or more cell display elements.

An image processing program according to still another aspect has characteristics of causing an information processing device to function as the image processing device according to one aspect by being executed in a control unit of the information processing device.

Advantageous Effects of Invention

According to the present invention, a cell display element depicted by a user is set to be in a state of being deleted or unadopted according to characteristics in appearance of at least one of the cell display element and an assumed cell area of a cell morphology image corresponding to the cell display element, and thus, a cell distribution image is generated. For this reason, for example, it is difficult to allow a variation to occur in a cell distribution image obtained between users. As a result thereof, it is possible to stably acquire an image accurately representing a distribution of an area where a specific portion of a cell is captured in an image capturing a cell morphology.

DESCRIPTION OF EMBODIMENTS

Figure 1:
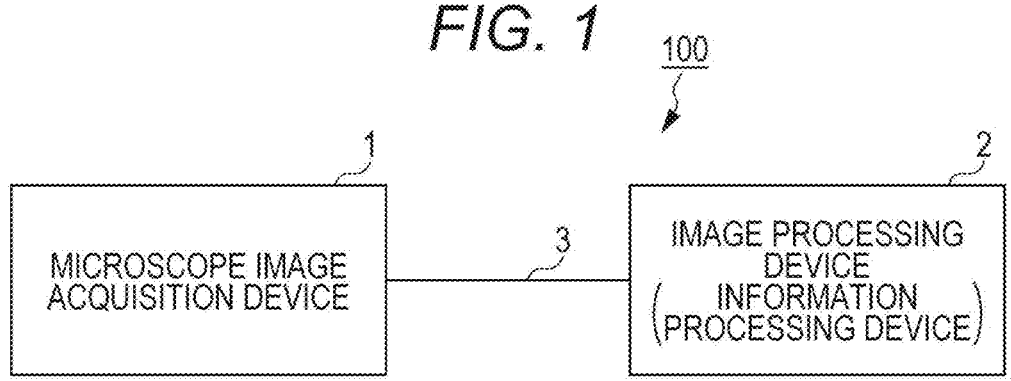
FIG. 1 is a diagram in which a schematic configuration of a pathological diagnosis support system according to one embodiment is exemplified.

Hereinafter, one embodiment and various modification examples of the present invention will be described on the basis of the drawings. Furthermore, in the drawings, the same reference numerals are applied to portions having similar configurations and functions, and in the following description, the repeated description will be omitted. In addition, the drawings are schematically illustrated, and a size, a positional relationship, or the like of various configurations each of the drawings can be suitably changed.

(1) One Embodiment

<(1-1) Summary of Pathological Diagnosis Support System>

FIG. 1 is a diagram illustrating one schematic configuration example of a pathological diagnosis support system 100 according to one embodiment. The pathological diagnosis support system 100, for example, performs analysis processing in which a microscope image capturing a tissue section of a biological object stained with a predetermined staining reagent is acquired, various image processings are performed with respect to the microscope image, and then, an analysis value relevant to an existence state of a specific biological substance of the tissue section is calculated.

Here, the microscope image, for example, includes an image capturing a cell morphology in the tissue section of the biological object (also referred to as a cell morphology image), and an image corresponding to the existence state of the specific biological substance in the tissue section of the biological object. The biological object, for example, may include animals in a broad sense, in which a human body or animals except for human beings, and both of the human body and the animals except for the human beings are included. In various image processings, for example, the analysis processing includes processing performed in the microscope image such that the analysis value relevant to the existence state of the specific biological substance is obtained from the microscope image with a high accuracy.

As illustrated in FIG. 1, the pathological diagnosis support system 100 includes a microscope image acquisition device 1, an image processing device 2, and a communication line 3 connecting the microscope image acquisition device 1 and the image processing device 2 together such that reception and transmission of data can be performed. The communication line 3, for example, may be a line in a wired manner, such as a cable, or may be a line in a wireless manner. Specifically, for example, a local area network (LAN) in which at least one manner of a wired manner and a wireless manner is adopted can be adopted as the communication line 3. In addition, the delivery of the data between the microscope image acquisition device 1 and the image processing device 2 may be performed by delivery using various media such as a storage medium.

<(1-2) Microscope Image Acquisition Device>

The microscope image acquisition device 1, for example, is an optical microscope with a known camera. In the microscope image acquisition device 1, an optical image of a tissue section on slide glass which is disposed on a stage is imaged, and thus, data of an image relevant to an enlarged image of the tissue section (also referred to as a microscope image) (also referred to as microscope image data) is acquired, and the microscope image data is transmitted to the image processing device 2. Furthermore, hereinafter, the microscope image data and the microscope image will be collectively referred to as a "microscope image".

Specifically, the microscope image acquisition device 1, for example, includes an irradiation unit, an image formation unit, an imaging unit, a communication I/F, and the like. The irradiation unit, for example, includes a light source, a filter, and the like, and irradiates the tissue section on the slide glass which is disposed on the stage with light. The image formation unit, for example, includes an ocular lens, an objective lens, and the like, and forms an image with transmitted light, reflected light, or fluorescent light emitted from the tissue section, according to the irradiation of the light with respect to the tissue section on the slide. The imaging unit, for example, is a camera including a charge coupled device (CCD) sensor and the like, and acquires the microscope image by imaging an optical image of the tissue section which is formed on an image formation surface by the image formation unit. The communication I/F transmits the microscope image to the image processing device 2.

In addition, the microscope image acquisition device 1 includes a bright field unit in which an irradiation unit and an image formation unit, suitable for bright field observation, are combined together, and a fluorescent unit in which an irradiation unit and an image formation unit, suitable for fluorescent observation, are combined together. Then, units to be used between the bright field unit and the fluorescent unit are switched, and thus, observation modes are switched between a mode of performing the bright field observation and a mode of performing the fluorescent observation. Accordingly, the microscope image acquired in the microscope image acquisition device 1, for example, includes a bright field image obtained according to the imaging in the bright field observation and a fluorescent image obtained according to the imaging in the fluorescent observation.

Figure 2:
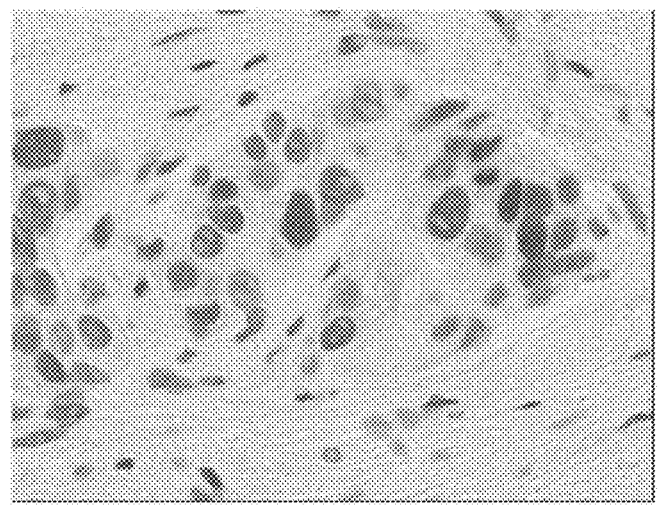
FIG. 2 is a diagram illustrating an example of a cell morphology image.

The "bright field image" is a microscope image obtained by performing enlarged image formation and imaging with respect to a tissue section stained with a predetermined staining reagent in a bright field of the microscope image acquisition device 1. Here, for example, a hematoxylin staining reagent (an H staining reagent) and a hematoxylin-eosin staining reagent (an HE staining reagent) can be adopted as the predetermined staining reagent. Hematoxylin (H) is a bluish-purple pigment, and stains a part of a cell nucleus, a bone tissue, and a cartilage tissue, and a serous component or the like (a basophilic tissue or the like). Eosin (E) is a red to pink pigment, and stains a cell cytoplasm, a bond tissue of a soft tissue, a red blood cell, a fibrin, and an endocrine granule or the like (an acidophilic tissue or the like). That is, in this embodiment, the bright field image is a cell morphology image capturing a cell morphology in a tissue section of a biological object stained with a predetermined staining reagent. FIG. 2 is a diagram illustrating an example of the cell morphology image. In the example of FIG. 2, in order to express the drawing with black and white, for the sake of convenience, a contrasting density of a color captured in the cell morphology image is represented by a gray contrasting density.

Figure 3:
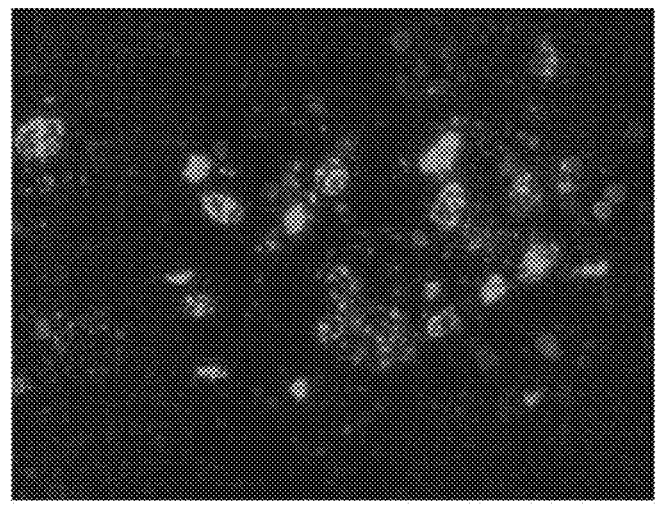
FIG. 3 is a diagram illustrating an example of a fluorescent image.

In addition, the "fluorescent image" is a microscope image obtained by irradiating a tissue section stained by using a predetermined fluorescent staining reagent with excitation light having a predetermined wavelength in the microscope image acquisition device 1 to emit fluorescent light, and then, by performing enlarged image formation and imaging with respect to the fluorescent light. Here, the fluorescent staining reagent, for example, is a staining reagent containing fluorescent substance-containing nanoparticles to which a biological substance recognition portion specifically bonded to and/or reacts with a specific biological substance is bonded. The fluorescent substance-containing nanoparticles are nanoparticles containing a fluorescent substance. The fluorescent light expressed in the fluorescent observation is generated by exciting the fluorescent substance-containing nanoparticles of the fluorescent staining reagent (specifically, the fluorescent substance), and represents the expression of the specific biological substance corresponding to the biological substance recognition portion in the tissue section. In particular, in a case of adopting the fluorescent substance-containing nanoparticles containing a fluorescent substance (also referred to as fluorescent particles), an expression amount of the specific biological substance can be calculated as not only a brightness of the fluorescent particles but also the number of particles, and can be accurately quantified. That is, in this embodiment, the fluorescent image is an image capturing the tissue section of the biological object in which the specific biological substance is stained with the fluorescent staining reagent, and is an image representing the existence state of the specific biological substance in the tissue section of the biological object. FIG. 3 is a diagram illustrating an example of the fluorescent image. In the example of FIG. 3, in order to express the drawing with black and white, for the sake of convenience, a portion in which the fluorescent light is emitted to the black background is represented as white.

<(1-3) Fluorescent Staining Reagent>

<(1-3-1) Fluorescent Substance>

For example, a fluorescent organic pigment, a quantum dot (semiconductor particles), and the like can be adopted as the fluorescent substance used in the fluorescent staining reagent. For example, a substance emitting light of visible light having a wavelength within a range of 400 nm to 1100 nm to near-infrared light at the time of being excited by ultraviolet light having a wavelength within a range of 200 nm to 700 nm to near-infrared light can be adopted as the fluorescent substance.

For example, fluorescein-based pigment molecules, rhodamine-based pigment molecules, Alexa. Fluor (manufactured by Life Technology Inc.)-based pigment molecules, BODIPY (manufactured by Life Technology Inc.)-based pigment molecules, cascade-based pigment molecules, coumarin-based pigment molecules, eosin-based pigment molecules, NBD-based pigment molecules, pyrene-based pigment molecules, Texas Red-based pigment molecules, and/or cyanine-based pigment molecules, and the like can be adopted as the fluorescent organic pigment.

Specifically, for example, one type of fluorescent organic pigment of 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxy fluorescein, naphthofluorescein, 5-carboxy-rhodamine, 6-carboxy-rhodamine, 5,6-dicarboxy-rhodamine, rhodamine 6G tetramethyl rhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (all are manufactured by Life Technology Inc.), methoxy coumarin, eosin, NBD, pyrene, Cy5, Cy5.5, and Cy7 can be adopted, or two types or more of fluorescent organic pigments thereof can be adopted by being mixed.

In addition, for example, one quantum dot of a quantum dot containing a compound of a group II-VI as a component (also referred to as a quantum dot of a group II-VI), a quantum dot containing a compound of a group III-V as a component (also referred to as a quantum dot of a group III-V), and a quantum dot containing an element of a group IV as a component (also referred to as a quantum dot of a group IV) can be adopted as the quantum dot, or two or more quantum dots thereof can be adopted by being mixed.

Specifically, for example, one type of quantum dot of CdSe, CdS, CdTe, ZnSe, ZnS, ZnTe, InP, InN, InAs, InGaP, GaP, GaAs, Si, and Ge can be adopted, or two types or more of quantum dots thereof can be adopted by being mixed. Furthermore, a quantum dot in which the quantum dot described above is set to a core, and a shell is disposed thereon may be adopted.

<(1-3-2) Fluorescent Substance-Containing Nanoparticles>

In the fluorescent substance-containing nanoparticles (the fluorescent particles), the fluorescent substance is dispersed in the nanoparticles, the fluorescent substance and the nanoparticles itself may be chemically bonded to each other, or may not be bonded to each other. For example, polystyrene, a polylactic acid, silica, melamine, and the like can be adopted as a material configuring the nanoparticles. Such fluorescent substance-containing nanoparticles, for example, can be prepared according to a known method.

Specifically, the silica nanoparticles containing the fluorescent organic pigment, for example, can be synthesized with reference to a synthesis method of FITC containing silica particles described in Langmuir Vol. 8, p. 2921 (1992). Furthermore, a desired fluorescent organic pigment is used instead of FITC, and thus, silica nanoparticles containing various fluorescent organic pigments can be synthesized. In addition, the polystyrene nanoparticles containing the fluorescent organic pigment can be prepared by using a copolymerization method using an organic pigment having a polymerizable functional group, described in U.S. Pat. No. 4,326,008 A (1982), an impregnating method of a fluorescent organic pigment with respect to polystyrene nanoparticles, described in U.S. Pat. No. 5,326,692 A (1992), or the like.

In addition, the silica nanoparticles containing the quantum dot, for example, can be synthesized with reference to a synthesis method of CdTe-containing silica nanoparticles, described in New Journal of Chemistry Vol. 33, p. 561 (2009). In addition, the polymer nanoparticles containing the quantum dot, for example, can be prepared by using an impregnating method of a quantum dot with respect to the polystyrene nanoparticles, described in Nature and Biotechnology Vol. 19, p. 631 (2001).

In general, an average particle diameter of the fluorescent substance-containing nanoparticles may be approximately 30 nm to 800 nm such that for example, ease of access with respect to antigen, and a signal of the fluorescent particles is not buried in the background noise (a camera noise and autogenic fluorescent light of a cell, and the like). In addition, in general, a variation coefficient representing a variation in a particle diameter of the fluorescent substance-containing nanoparticles, for example, may be less than or equal to 20%. Furthermore, in the average particle diameter, for example, sectional areas of 1000 particles are measured from an image capturing a sectional surface of a plurality of particles obtained by photographing using a scanning electron microscope (SEM), and when each measurement value is set to an area of a circle, the diameter of the circle is set to a particle diameter, and an arithmetic average thereof can be calculated as the average particle diameter.

<(1-3-3) Biological Substance Recognition Portion>

The biological substance recognition portion is a portion which is specifically bonded to and/or reacts with a biological substance, which is an object. For example, a protein (a peptide), a nucleic acid (an oligonucleotide and a polynucleotide), an antibody, and the like can be representatively adopted as the biological substance, which is the object. That is, an antibody recognizing the protein described above as an antigen, other proteins or the like specifically bonded to the protein described above, and a nucleic acid or the like having a base sequence hybridized to the nucleic acid described above can be adopted as the substance bonded to the biological substance, which is the object.

Specifically, an anti-HER2 antibody specifically bonded to HER2, which is a protein existing on a cell surface, an anti-ER antibody specifically bonded to an estrogen receptor (ER) existing in a cell nucleus, an antiactine antibody specifically bonded to an actin forming a cell skeleton, and the like can be adopted as the substance bonded to the biological substance, which is the object. Among them, a substance in which the anti-HER2 antibody and the anti-ER antibody are bonded to the fluorescent substance-containing nanoparticles can be used for medication selection of a breast cancer.

For example, a covalent bond, an ion bond, a hydrogen bond, a coordination bond, a physical adsorption and/or a chemical adsorption, and the like can be adopted as an aspect of bonding the biological substance recognition portion and the fluorescent substance-containing nanoparticles together. In a case where a bonding force is strong, such as a covalent bond, the bonding can be stabilized. In addition, the biological substance recognition portion and the fluorescent substance-containing nanoparticles may be connected to each other by organic molecules. For example, in order to suppress non-specific adsorption with respect to the biological substance, a polyethylene glycol chain or SM (PEG) 12 (manufactured by Thermo Fisher Scientific K.K.) can be adopted as the organic molecules.

In a case where the biological substance recognition portion is bonded to the fluorescent substance-containing silica nanoparticles, the similar procedure can be applied even in a case where the fluorescent substance is any one of a fluorescent organic pigment and a quantum dot. For example, in the bonding, a silane coupling agent which is a compound widely used for bonding an inorganic substance and an organic substance together can be adopted. Such a silane coupling agent is a compound which has an alkoxysilyl group applying a silanol group on one end of molecules by hydrolysis, and has a functional group (for example, a carboxyl group, an amino group, an epoxy group, an aldehyde group, and the like) on the other end, and is bonded to an inorganic substance through an oxygen atom of the silanol group described above. Specifically, mercapto propyl triethoxy silane, glycidoxy propyl triethoxy silane, aminopropyl triethoxy silane, a silane coupling agent having a polyethylene glycol chain (for example, PEG-silane no. SIM6492.7, manufactured by Gelest, Inc.), and the like are adopted as such a silane coupling agent. In a case of using the silane coupling agent, for example, two types or more of silane coupling agents may be used together.

Here, a known procedure can be adopted as a reaction procedure between the fluorescent organic pigment-containing silica nanoparticles and the silane coupling agent. For example, first, the obtained fluorescent organic pigment-containing silica nanoparticles are dispersed in pure water, aminopropyl triethoxy silane is added thereto, and a reaction is performed at a room temperature for 12 hours. The reaction is ended, and then, fluorescent organic pigment-containing silica nanoparticles of which a front surface is modified with an aminopropyl group can be acquired by centrifugal separation or filtration. Subsequently, an amino group reacts with a carboxyl group in an antibody, and thus, the antibody can be bonded to the fluorescent organic pigment-containing silica nanoparticles through an amide bond. As necessary, a condensation agent such as 1-ethyl- 3-[3-dimethylaminopropyl] carbodiimide Hydrochloride (EDC): Pierce (registered trademark), manufactured by Thermo Fisher Scientific Inc.) may be used.

In addition, as necessary, a linker compound having a portion which can be directly bonded to fluorescent organic pigment-containing silica nanoparticles modified with organic molecules and a portion which can be bonded to a molecular target substance may be adopted. As a specific example, in a case of using sulfo-sulfosuccinimidyl 4[N-maleimidomethyl]-cyclohexane-1-carboxylate (SMCC): Pierce (registered trademark), manufactured by Thermo Fisher Scientific Inc.) having both of a portion selectively reacting with an amino group and a portion selectively reacting with a mercapto group, an amino group of fluorescent organic pigment-containing silica nanoparticles modified with aminopropyl triethoxy silane and a mercapto group in the antibody are bonded together, and thus, fluorescent organic pigment-containing silica nanoparticles to which an antibody is bonded can be acquired.

In a case where a biological substance recognition portion is bonded to the fluorescent substance-containing polystyrene nanoparticles, the similar procedure can be applied, even in a case where the fluorescent substance is any one of a fluorescent organic pigment and a quantum dot. That is, a fluorescent organic pigment or a quantum dot is impregnated in polystyrene nanoparticles having a functional group such as an amino group, and thus, fluorescent substance-containing polystyrene nanoparticles having a functional group can be acquired. Hereinafter, EDC or sulfo-SMCC is used, and thus, fluorescent substance-containing polystyrene nanoparticles to which an antibody is bonded can be acquired.

In a case where the biological substance recognition portion is bonded to the fluorescent substance-containing melamine nanoparticles, a procedure similar to a case where the biological substance recognition portion is bonded to the fluorescent substance-containing silica nanoparticles can be applied. In addition, in order to further improve reactivity, the number of surface amino groups may increase by allowing melamine nanoparticles to react with a polyfunctional amine compound in advance.

Examples of the antibody recognizing a specific antigen include M. actine, M.S. actine, S.M. actine, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, CD99, MIC2, CD138, chromogranin, c-KIT, c-MET, collagen type IV, Cox-2, cyclin D1, keratin, cytokeratin (high molecular weight), pankeratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, a factor VIII related antigen, fascin, FSH, galectin-3, gastrin, GFAP, glucagon, glycophorin A, granzyme B, hCG, hGH, *Helicobacter pylori*, an HBc antigen, an HBs antigen, a hepatocyte specific antigen, HER2, HSV-I, HSV-II, HHV-8, IgA, IgG, IgM, IGF-1R, inhibin, insulin, a Kappa L chain, Ki67, a lambda L chain, LH, lysozyme, macrophage, melan A, MLH-1, MSH-2, myeloperoxidase, myogenin, myoglobin, myosin, neurofilament, NSE, p27 (Kip1), p53, p53, P63, PAX 5, PLAP, *Pneumocystis carinii*, podoplanin (D2-40), PGR, prolactin, PSA, prostatic acid phosphatase, renal cell carcinoma, S100, somatostatin, spectrin, synaptophysin, TAG-72, TdT, thyroglobulin, TSH, TTF-1, TRAcP, tryptase, villin, vimentin, WT1, Zap-70, and the like.

<(1-4) Staining Method of Fluorescent Staining Reagent and Acquisition Method of Fluorescent Image>

Hereinafter, a staining method of a tissue specimen will be described, but the present invention is not limited to the tissue specimen, and can be applied to a specimen of a cell fixed onto a substrate, or the like. In addition, the tissue specimen to which the staining method described below can be applied, for example, can be prepared by a known method.

<(1-4-1) Deparaffinization Step>

The tissue specimen is dipped in a container into which xylene is put, and paraffin is removed. At this time, a treatment temperature, for example, may be a suitable temperature such as a room temperature, and dipping time, for example, may be longer than or equal to 3 minutes and shorter than or equal to 30 minutes. In addition, as necessary, xylene may be exchanged during the dipping.

Next, the tissue specimen is dipped in a container into which ethanol is put, and xylene is removed. At this time, a treatment temperature, for example, may be a suitable temperature such as a room temperature, and dipping time, for example, may be longer than or equal to 3 minutes and shorter than or equal to 30 minutes. In addition, as necessary, ethanol may be exchanged during the dipping.

Next, the tissue specimen is dipped in a container into which water is put, and ethanol is removed. At this time, a treatment temperature, for example, may be a suitable temperature such as a room temperature, and dipping time, for example, may be longer than or equal to 3 minutes and shorter than or equal to 30 minutes. In addition, as necessary, water may be exchanged during the dipping.

<(1-4-2) Activation Treatment>

An activation treatment of the biological substance, which is the object, is performed according to a known method. In the activation treatment, a citrate buffer solution of 0.01 M (pH 6.0), an EDTA solution of 1 mM (pH 8.0), urea of 5%, a tris-hydrochloric acid buffer solution of 0.1 M, and the like can be used as an activation liquid. At this time, an autoclave, a microwave, a pressure cooker, a water bath, and the like can be adopted as a heating device. A treatment temperature, for example, may be a suitable temperature such as a room temperature. Specifically, a condition can be adopted in which a treatment temperature is 50° C. to 130° C., and treatment time is 5 minutes to 30 minutes.

Next, the tissue specimen which has been subjected to an activation treatment is dipped in a container into which phosphate buffered saline (PBS) is put, and is washed. At this time, a treatment temperature, for example, may be a suitable temperature such as a room temperature, and dipping time, for example, may be longer than or equal to 3 minutes and shorter than or equal to 30 minutes. In addition, as necessary, PBS may be exchanged during the dipping.

<(1-4-3) Staining of Fluorescent Substance-Containing Nanoparticles to which Biological Substance Recognition Portion is Bonded>

A PBS dispersion liquid of the fluorescent substance-containing nanoparticles to which the biological substance recognition portion is bonded is placed on the tissue specimen, and reacts with the biological substance, which is the object. By changing the biological substance recognition portion to which the fluorescent substance-containing nanoparticles is bonded, staining corresponding to the various biological substance can be performed. In a case of adopting fluorescent substance-containing nanoparticles to which several types of biological substance recognition portions are bonded, each PBS dispersion liquid of the fluorescent substance-containing nanoparticles may be mixed in advance, or may be sequentially placed on the tissue specimen. At this time, a treatment temperature, for example, may be suitable temperature such as a room temperature, and dipping time, for example, may be longer than or equal to 30 minutes and shorter than or equal to 24 hours. Here, for example, a known blocking agent such as BSA-containing PBS may be dropped with respect to the tissue specimen, before the staining of the fluorescent substance-containing nanoparticles is performed.

Next, the tissue specimen which has been stained is dipped in a container into which PBS is put, and unreacted fluorescent substance-containing nanoparticles are removed. At this time, a treatment temperature, for example, may be a suitable temperature such as a room temperature, and dipping time, for example, may be longer than or equal to 3 minutes and shorter than or equal to 30 minutes. In addition, as necessary, PBS may be exchanged during the dipping.

Then, the tissue specimen is sealed by placing cover glass on the tissue specimen which has been stained. At this time, as necessary, a commercially available sealing agent may be used.

Furthermore, in order to obtain a bright field image, in a case where the staining is performed by an HE staining reagent, HE staining may be performed before the tissue specimen is sealed by the cover glass.

<(1-4-4) Acquisition of Fluorescent Image>

The microscope image acquisition device 1 is used with respect to the tissue specimen as the stained tissue section, and a wide-field microscope image (the fluorescent image) is acquired. At this time, in the microscope image acquisition device 1, an excitation light source and an optical filter for fluorescent detection are selected, corresponding to an absorption maximum wavelength and a fluorescent wavelength of the fluorescent substance used in the staining reagent.

<(1-5) Image Processing Device>

The image processing device 2 receives a microscope image transmitted from the microscope image acquisition device 1, such as a cell morphology image and a fluorescent image, and performs image processing with respect to the microscope image. The image processing device 2 is realized by executing a predetermined program in an information processing device.

<(1-5-1) Functional Configuration of Information Processing Device>

Figure 4:
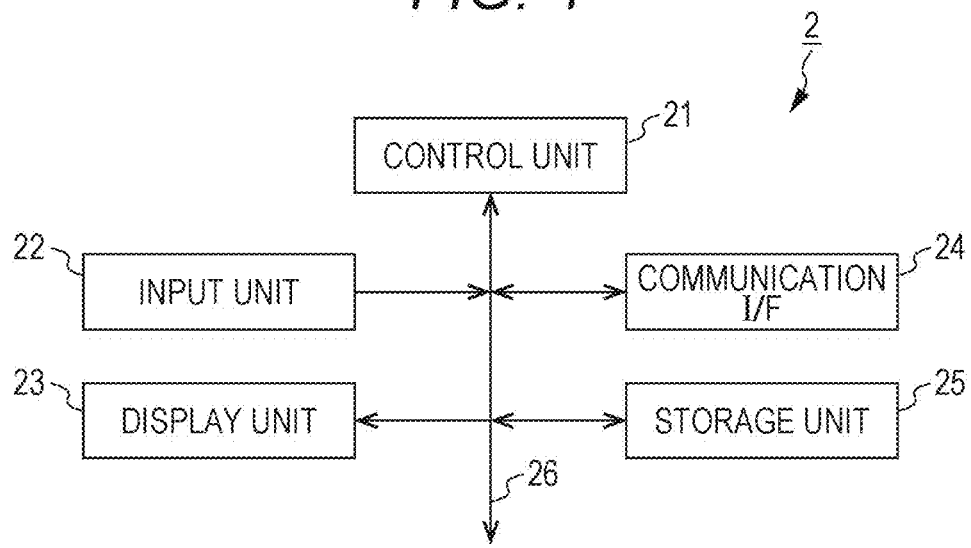
FIG. 4 is a block diagram schematically illustrating a functional configuration of an information processing device.

FIG. 4 is a block diagram schematically illustrating a functional configuration of the information processing device which realizes the function of the image processing device 2. As illustrated in FIG. 4, the information processing device, for example, includes a control unit 21, an input unit 22, a display unit 23, a communication I/F 24, a storage unit 25, and the like. Then, units 21 to 25 are connected to each other through a bus 26 such that data can be received from and transmitted to each other.

The control unit 21 is an electric circuit provided with a processor, a memory, and the like. Here, for example, a central processing device (CPU) or the like can be adopted as the processor, and a random access memory (RAM), which is a volatile memory, or the like can be adopted as the memory. The control unit 21 executes an image processing program P1 (FIG. 5) stored in the storage unit 25, and thus, causes the information processing device to function as the image processing device 2.

The input unit 22 inputs a signal according to an operation of an operator using the image processing device 2, who is a user. Here, the input unit 22, for example, may be an operation unit into which a signal according to the operation of the user (also referred to as an operation signal) is input, or may be a sound input unit into which a signal according to the sound of the user (also referred to as a sound signal) is input. A keyboard including a character input key, a number input key, various function keys, and the like, and a pointing device such as a mouse or a touch pen can be included in the operation unit. According to the operation unit, for example, an operation signal according to the pressing of the key on the keyboard, and an operation signal according to the operation of the pointing device can be input into the control unit 21.

The display unit 23 displays various images according to the signal input from the control unit 21. The display unit 23, for example, includes a display device such as a cathode ray tube (CRT) or a liquid crystal display (LCD).

The communication I/F 24 is an interface for performing reception and transmission of data with respect to the external device which is positioned on the outside of the image processing device 2. The external device, for example, includes the microscope image acquisition device 1. For this reason, the communication I/F 24, for example, functions as a receiving unit receiving a microscope image such as a cell morphology image and a fluorescent image from the microscope image acquisition device 1. Furthermore, for example, a configuration may be adopted in which the image processing device 2 includes a LAN adapter, a router, and the like, and is connected to the external device through a communication network such as a LAN.

The storage unit 25 stores various programs, various data items, and the like. The storage unit 25, for example, can be configured of a hard disk drive (HDD), a non-volatile semiconductor memory, or the like.

<(1-5-2) Functional Configuration of Image Processing Device>

Figure 5:
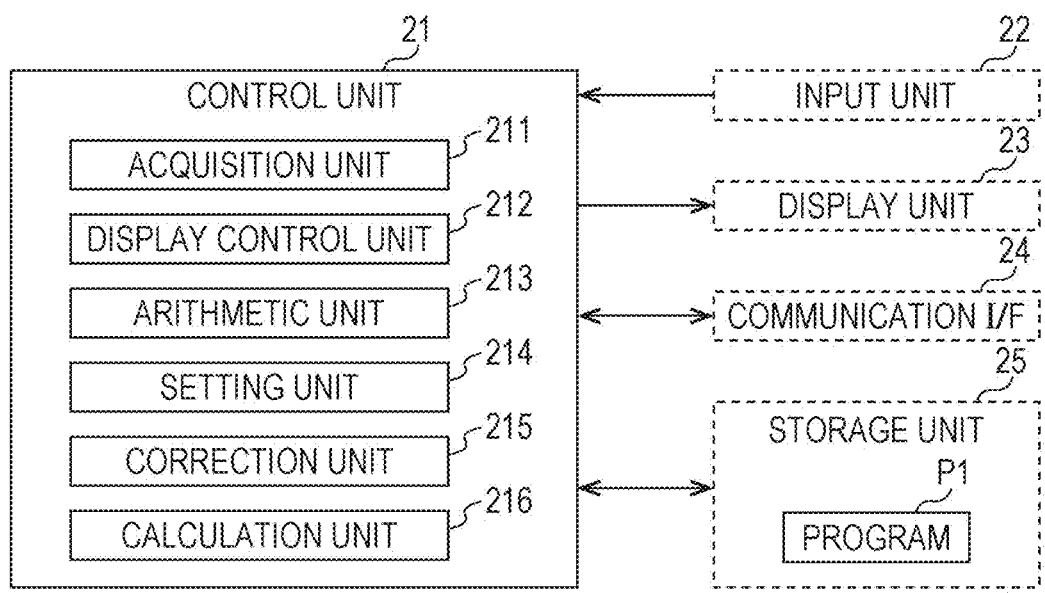
FIG. 5 is a block diagram in which a functional configuration realized by a control unit is exemplified.

FIG. 5 is a block diagram in which a functional configuration realized by the control unit 21 of the image processing device 2 is exemplified. As illustrated in FIG. 5, the image processing device 2 includes an acquisition unit 211, a display control unit 212, an arithmetic unit 213, a setting unit 214, a correction unit 215, and a calculation unit 216, as the functional configuration realized in the control unit 21.

The acquisition unit 211 acquires a virtual cell distribution image and a bright point distribution image.

The virtual cell distribution image is an image in which a distribution of an area to be assumed that a specific portion of a cell is captured in a cell morphology image capturing a plurality of cell morphologies in a tissue section of a biological object stained with a predetermined staining reagent (also referred to as an assumed cell area) is represented by a plurality of elements (also referred to as a cell display element). That is, the virtual cell distribution image can be acquired from the cell morphology image.

Figure 6:
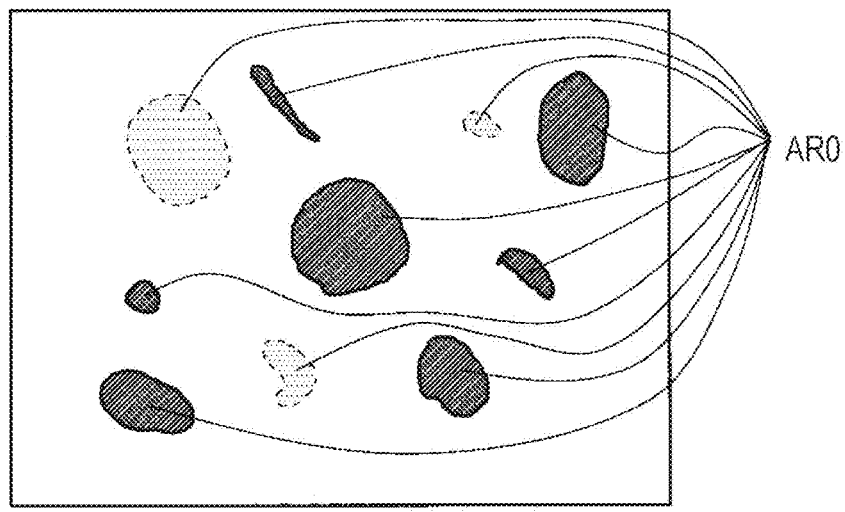
FIG. 6 is a diagram schematically illustrating an example of the cell morphology image.

Here, as described above, the cell morphology image, for example, is a bright field image capturing a cell morphology in the tissue section of the biological object stained with the predetermined staining reagent. FIG. 6 is a diagram schematically illustrating an example of the cell morphology image. The cell morphology image, for example, is an image capturing a color contrasting density according to the staining relevant to the cell morphology. For example, in a case where the specific portion of the cell is stained with blue by an H staining reagent, the cell morphology image exhibits a blue contrasting density. In the example of FIG. 6, in order to express the drawing with black and white, for the sake of convenience, a color contrasting density of an assumed cell area AR0 to be assumed as being captured in the cell morphology image is schematically represented by the type and the denseness of black and white hatching. That is, in the example of FIG. 6, the entire assumed cell area AR0 is hatched. In addition, in the example of FIG. 6, the unclear outline of the assumed cell area is represented by a broken line.

Figure 7:
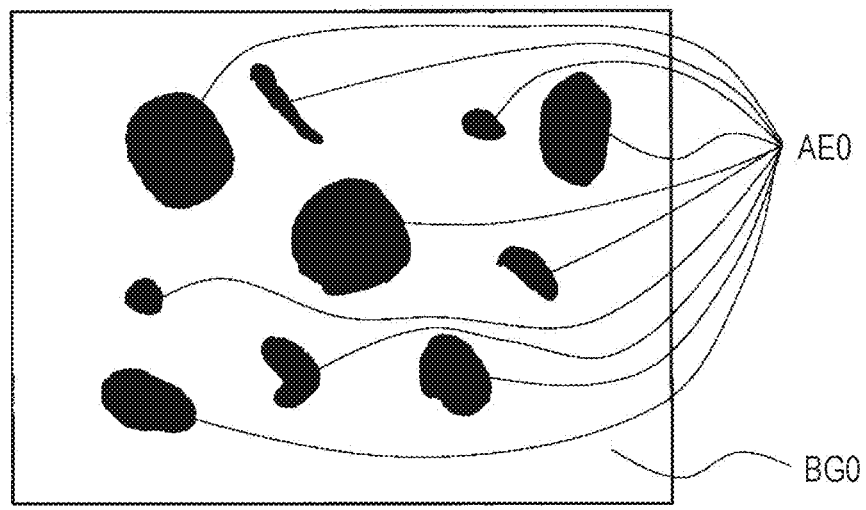
FIG. 7 is a diagram schematically illustrating an example of a virtual cell distribution image.

FIG. 7 is a diagram schematically illustrating an example of a virtual cell morphology image acquired from the cell morphology image schematically illustrated in FIG. 6. For example, an image in an aspect where the distribution of the assumed cell area to be assumed that the specific portion is captured, and a distribution of a residual area to be assumed that the specific portion is not captured can be discriminated from each other, in the cell morphology image, can be adopted as the virtual cell distribution image. Specifically, for example, a portion AE0 corresponding to the assumed cell area is represented by a cell display element with a first color or first hatching, and a residual portion BG0 other than the portion AE0 is depicted with a second color or second hatching, which is different from the cell display element, as the background. Here, for example, blue, gray, or the like can be adopted as the first color, and for example, white, black, or the like can be adopted as the second color. In the example of FIG. 7, in order to express the drawing with black and white, for the sake of convenience, black is adopted as the first color, and white is adopted as the second color. That is, in the example of FIG. 7, the portion AE0 corresponding to the entire assumed cell area to be assumed that the specific portion is captured is painted with black, and a residual portion BG1 is painted with white.

Here, for example, the virtual cell distribution image can be acquired according to a combination of predetermined image processing, in which the cell morphology image is set as a target, and the drawing of the user (that is, correction), or the drawing of the user. In the example of FIG. 7, a portion corresponding to an assumed cell area detected by the predetermined image processing in which the cell morphology image is set as the target, and a portion corresponding to an assumed cell area drawn by the user in addition to the assumed cell area, are represented by a cell display element painted with black. Furthermore, as the cell display element, for example, it is preferable that the portion AE0 corresponding to the assumed cell area and the residual portion BG1 other than the portion AE0 can be discriminated from each other. For this reason, for example, a curve which is depicted along the outline portion of the portion corresponding to the assumed cell area by the user may be adopted as the cell display element, a curve which is automatically depicted along the outline portion of the portion corresponding to the assumed cell area detected by the predetermined image processing in which the cell morphology image is set as the target, and the like may be adopted.

Figure 8:
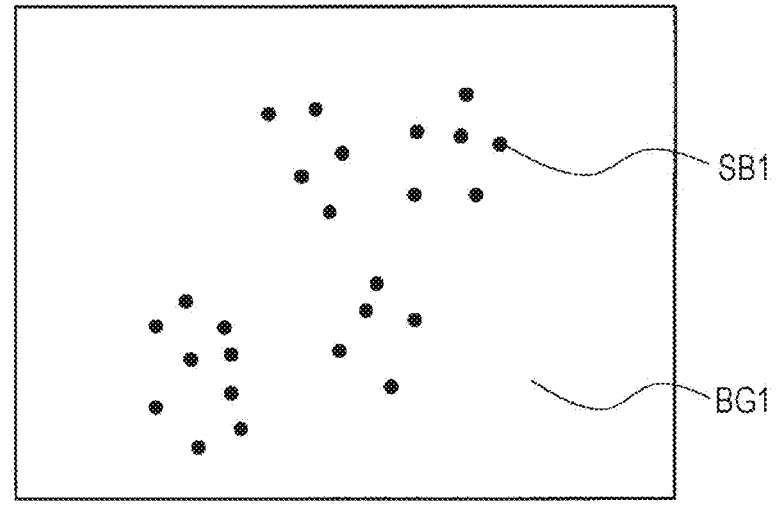
FIG. 8 is a diagram schematically illustrating an example of a bright point distribution image.

The bright point distribution image is an image illustrating a distribution of a fluorescent bright point relevant to specific wavelength of the fluorescent image capturing the tissue section of the biological object in which the specific biological substance is stained with the fluorescent staining reagent. FIG. 8 is a diagram illustrating an example of the bright point distribution image. For example, an image represented by an aspect, in which a distribution of an area where the bright point relevant to the specific wavelength is captured, and a distribution of a residual area where the fluorescent bright point relevant to the specific wavelength is not captured can be discriminated from each other, with respect to the fluorescent image, can be adopted as the bright point distribution image.

Specifically, for example, a portion SB1 corresponding to an area to be assumed that the fluorescent bright point is captured, and a specific substance exists (also referred to as a fluorescent bright point area) is represented by a display element with a third color or third hatching (also referred to as a bright point display element), and the residual portion BG1 other than the portion SB1 is depicted with a fourth color or fourth hatching, which is different from the bright point display element, as the background. Here, for example, red or the like can be adopted as the third color, for example, white, black, or the like can be adopted as the fourth color. In the example of FIG. 8, in order to express the drawing with black and white, for the sake of convenience, black is adopted as the third color, and white is adopted as the fourth color. That is, in the example of FIG. 8, the portion SB1 corresponding to the area where the fluorescent bright point is captured is painted with black, and the residual portion BG1 is painted with white.

A plurality of cell display elements in the virtual cell distribution image, for example, are capable of including a cell display element which is automatically obtained by predetermined image processing in which a cell morphology image input from the communication I/F 24 is set as a target. In addition, a plurality of bright point display elements in the bright point distribution image, for example, can be automatically acquired by the other predetermined image processing in which a fluorescent image input from the communication I/F 24 is set as a target.

For example, processing in which an area to be assumed that the specific portion is captured in the cell morphology image is detected by at least one of binarization such as a processing discriminant analysis method and a P-tile method, and clustering such as a k average method and an EM algorithm, can be adopted as the predetermined image processing. In addition, for example, processing in which an area to be assumed that the specific portion is captured is detected in the cell morphology image may be adopted. Further, in the acquisition unit 211, an area satisfying the other criteria such as a degree of circularity, a size, and a color in the cell morphology image may be detected as the assumed cell area according to the results of the binarization, the clustering, and the machine learning, among areas detected once from the cell morphology image.

For example, processing in which a color component according to the specific wavelength of the fluorescent bright point is extracted from the fluorescent image, threshold value processing of deleting a portion of less than a threshold value relevant to a denseness is performed with respect to the fluorescent image after the color component is extracted, and thus, a binary image is generated, can be adopted as the other image processing. Here, for example, in a case where a wavelength of light emitted from the fluorescent particles is 550 nm, only a fluorescent bright point having the wavelength component can be extracted as an image. Here, the binary image to be generated corresponds to the bright point distribution image. Furthermore, in the other image processing, processing of removing autogenic fluorescent light of the cell and a noise component such as the other unnecessary signal component may be performed before the threshold value processing is performed.

In addition, the plurality of cell display elements in the virtual cell distribution image include one or more cell display elements depicted according to the signal input from the input unit 22 by the user. Here, for example, one or more cell display elements are depicted according to the signal input from the input unit 22 by the user in a state where the cell morphology image is displayed on the display unit 23, and thus, a virtual cell distribution image is acquired.

For example, an aspect is considered in which one or more cell display elements are added to an image obtained by the predetermined image processing from the cell morphology image (also referred to as a basic cell distribution image) by the user. Here, the basic cell distribution image is an image which is the basis of the virtual cell distribution image where a distribution of at least one assumed cell area is represented by at least one cell display element. In this case, for example, in order to represent a distribution of an assumed cell area other than the assumed cell area to be detected by performing the predetermined image processing with respect to the cell morphology image (also referred to as a detected cell area) (also referred to as a non-detection cell area) according to a predetermined signal input by the input unit 22, a display element corresponding to at least the outline portion of the non-detection cell area may be added to the basic cell distribution image. The predetermined signal may be set in advance.

FIGS. 9 to 13 are diagrams in which an aspect of acquiring a virtual cell distribution image from the cell morphology image schematically illustrated in FIG. 6 is schematically exemplified.

Figure 9:
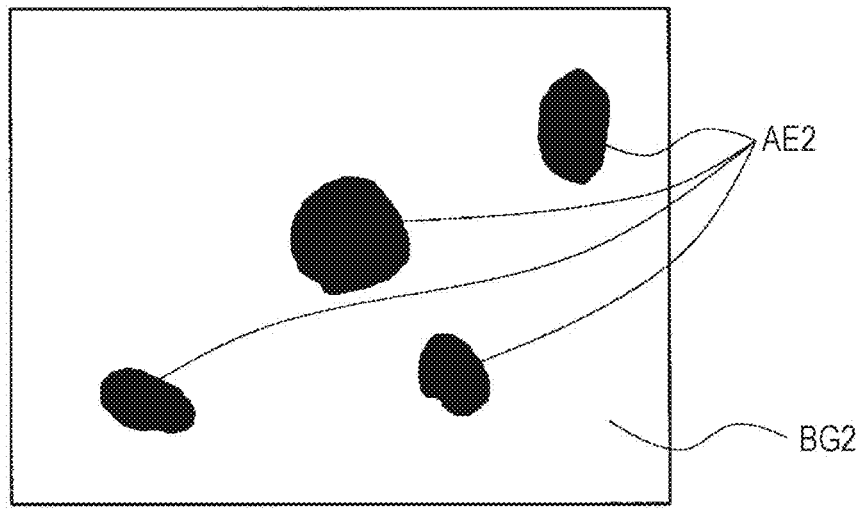
FIG. 9 is a diagram illustrating an example of a basic cell distribution image.

Here, first, for example, the assumed cell area (the detected cell area) is detected by performing the predetermined image processing with respect to the cell morphology image illustrated in FIG. 6, and as illustrated in FIG. 9, the basic cell distribution image is acquired in which a portion AE2 corresponding to the detected cell area is represented by the cell display element. In FIG. 9, a portion painted with black represents the cell display element. In addition, FIG. 10 illustrates an aspect in which the basic cell distribution image obtained by the predetermined image processing is superimposed on the cell morphology image.

Figure 10:
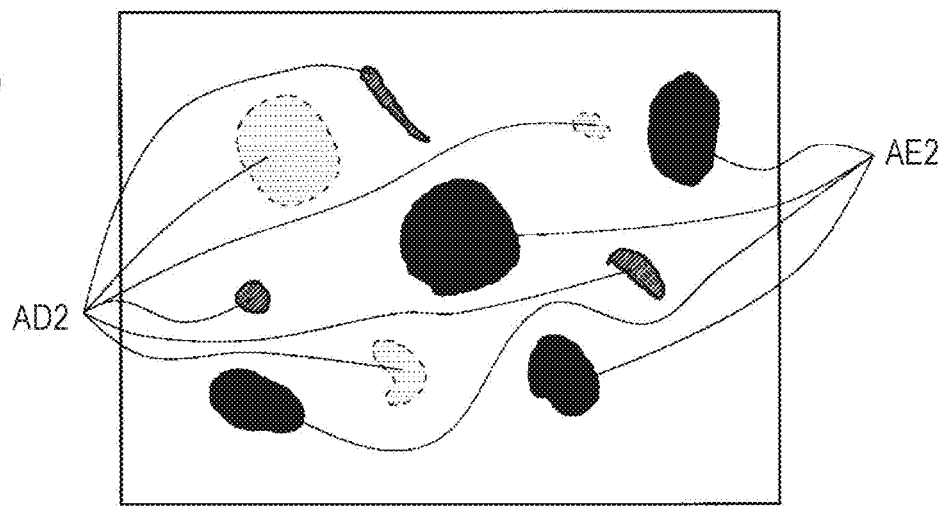
FIG. 10 is a diagram illustrating an example in which the basic cell distribution image is superimposed on the cell morphology image.
Figure 11:
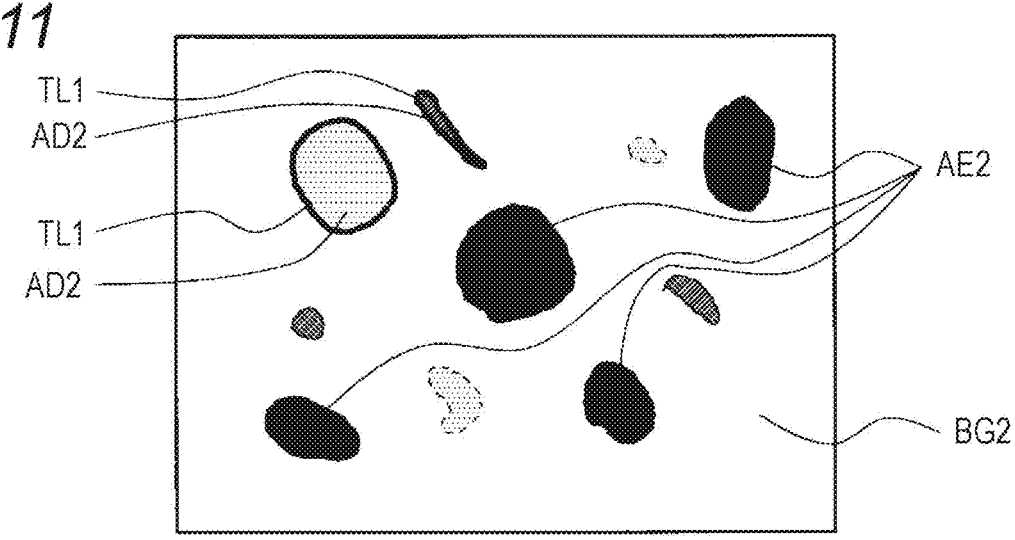
FIG. 11 is a diagram schematically illustrating an aspect in which a display element along an outline portion of an assumed cell area is depicted on the cell morphology image by a user.
Figure 12:
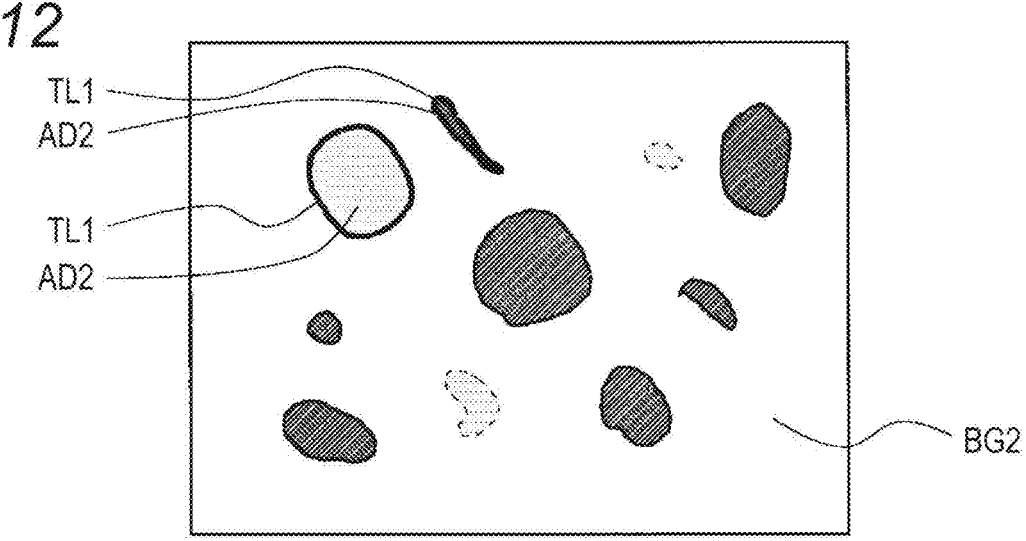
FIG. 12 is a diagram schematically illustrating an aspect in which the display element along the outline portion of the assumed cell area is depicted on the cell morphology image by the user.

Next, for example, as illustrated in FIG. 10, a curve along the outline portion of the portion AD2 corresponding to the non-detection cell area is depicted on the cell morphology image in a case where the cell morphology image is displayed on the display unit 23, according to the operation or the like of the input unit 22 by the user. FIG. 11 illustrates an aspect in which a thick curve TL1 along the outline of the portion AD2 corresponding to the non-detection cell area is depicted on the cell morphology image. At this time, for example, in the display unit 23, as illustrated in FIG. 11 and FIG. 12, the curve TL1 along the outline portion of the portion AD2 corresponding to the non-detection cell area can be depicted while a state where the cell display element is displayed to be superimposed on the cell morphology image (for example, FIG. 11) and a state where only the cell morphology image is displayed (for example, FIG. 12) are switched, according to the operation or the like of the input unit 22 by the user. Specifically, for example, a mouse pointer is moved along the outline portion of the non-detection cell area while a left button of the mouse is pressed, and thus, the curve can be depicted on a trajectory where the mouse pointer is moved.

Figure 13:
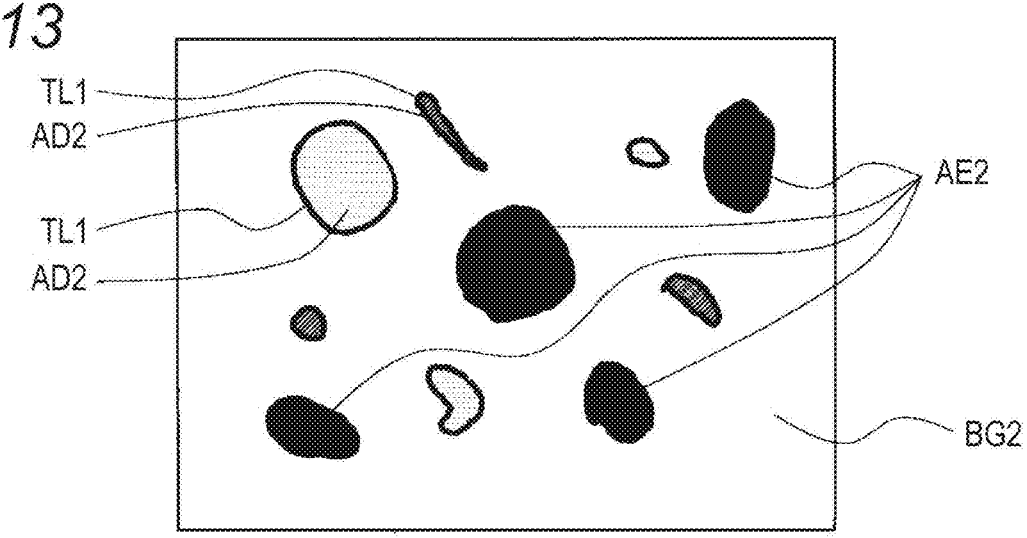
FIG. 13 is a diagram schematically illustrating an example in which the display element along the outline portion of the assumed cell area is depicted on the cell morphology image by the user.

Accordingly, for example, as illustrated in FIG. 13, the portions AE2 and AD2 corresponding to the assumed cell area, and a residual portion BG2 other than the portions AE2 and AD2 can be discriminated from each other. Specifically, in the example of FIG. 13, the portion AE2 corresponding to the assumed cell area (the detected cell area) detected by the predetermined image processing in which the cell morphology image is set as the target can be painted with black, and the outer edge of the portion AD2 corresponding to the residual assumed cell area (the non-detection cell area) can be depicted by a curve of the black thick line TL1 by the user.

The display control unit 212 displays various images on the display unit 23. Various images, for example, include the cell morphology image, the basic cell distribution image, the virtual cell distribution image, the cell distribution image, and the like. Here, for example, data relevant to various images is output to the display unit 23 from the display control unit 212, and thus, various images can be displayed on the display unit 23.

The arithmetic unit 213 obtains a value relevant to one type or more characteristics in appearance of the assumed cell area (the non-detection cell area) corresponding to the cell display element (also referred to as a characteristic value) in the cell morphology image, with respect to each of one or more cell display elements depicted by the user in the virtual cell distribution image. Here, one type or more characteristics in appearance, for example, are capable of including at least one characteristic of a size, a denseness, and a shape, with respect to the non-detection cell area. Accordingly, in the correction unit 215 described below, for example, processing can be realized in which an assumed cell area satisfying one or more conditions of three conditions that the area is small, the color is pale, and the shape is not round is not officially adopted as a cell area. As a result thereof, in the cell morphology image capturing the cell morphology, a cell distribution image accurately representing the distribution of the cell area where the specific portion of the cell is captured can be stably acquired.

Specifically, the characteristic relevant to the size, for example, is capable of including one type or more characteristics of a plurality of characteristics such as an area, a circumferential length, a length of a long axis, and a length of a short axis, with respect to the non-detection cell area. In addition, the characteristic relevant to the denseness, for example, is capable of including one type or more characteristics of a color phase (H: hue), a luminosity (V: value or B: brightness), a chromaticness (S: saturation), and a color difference (Cr and Cb), with respect to the non-detection cell area. In addition, the characteristic relevant to the shape, for example, is capable of including one type or more characteristics of a degree of circularity, a flatness ratio, and an aspect ratio, with respect to the non-detection cell area.

Here, the non-detection cell area, for example, can be recognized on the basis of the display element or the like which designates the outline portion added by the user, in the virtual cell distribution image.

The area of the non-detection cell area, for example, can be recognized by the number of pixels or the like configuring the non-detection cell area. The circumferential length of the non-detection cell area, for example, can be recognized by the length or the like of the display element which designates the outline portion of the non-detection cell area. The lengths of the long axis and the short axis of the non-detection cell area, for example, can be respectively recognized as a length in which straight lines at various angles intersect with the non-detection cell area while being shifted little by little, and thus, a distance between the straight lines and the non-detection cell area in an intersection state is maximized and minimized.

The color phase (H), the luminosity (V or B), the chromaticness (S), and the color difference (Cr and Cb) of the non-detection cell area, for example, can be calculated from a pixel value of a pixel configuring the non-detection cell area (for example, a pixel value relevant to three colors of RGB) according to a known conversion expression. Here, for example, the pixel values of three colors of red (R), green (G), and blue (B) are set to Vr, Vg, and Vb, and in the pixel values Vr, Vg, and Vb, a maximum value is set to Vmax, and a minimum value is set to Vmin.

At this time, the color phase (H) can be calculated by an expression of tan $H=\sqrt{3}\times(Vg-Vb)/(2Vr-Vg-Vb)$. In addition, for example, the color phase (H) may be calculated according to calculation rules of [i] to [iii] described below.

[i] In a case where Vr is the maximum value Vmax, the color phase (H) can be calculated by an expression of $H=60\times\{(Vg-Vb)/(Vmax-Vmin)\}$.

[ii] In a case where Vg is the maximum value Vmax, the color phase (H) can be calculated by an expression of $H=60\times\{(Vb-Vr)/(Vmax-Vmin)\}+120$.

[iii] In a case where Vb is the maximum value Vmax, the color phase (H) can be calculated by an expression of $H=60\times\{(Vr-Vg)/(Vmax-Vmin)\}+240$.

Furthermore, in a case where a relational expression of $Vr=Vg=Vb$ is established, the color phase (H) is zero (0).

In addition, the chromaticness (S), for example, can be calculated by an expression of $S=(Vmax-Vmin)/Vmax$. The luminosity (V or B), for example, can be calculated by an expression of $V=Vmax$ or $B=Vmax$. The color difference (Cr and Cb), for example, can be calculated by an expressions of $Cr=0.500Vr-0.419Vg-0.081Vb$ and $Cb=-0.169Vr-0.332Vg+0.500Vb$.

In a case where an area of the non-detection cell area is set to S, and a circumferential length of the non-detection cell area is set to L, a degree of circularity (Dc) of the non-detection cell area, for example can be calculated by an expression of $Dc=4\pi\times S/L^2$. In a case where a long diameter is set to a, and a short diameter is set to b, a flatness ratio (F: flattening) of the non-detection cell area, for example, can be calculated by an expression of $F=(a-b)/a$. In a case where the long diameter is set to a, and the short diameter is set to b, an aspect ratio (AR), for example, can be calculated by an expression of $Ar=a/b$. Furthermore, the long diameter is a length of the non-detection cell area on a long axis, and the short diameter is a length of the non-detection cell area on a short axis.

In addition, in the arithmetic unit 213, as necessary, the characteristic value relevant to one type or more characteristics in appearance of the assumed cell area corresponding to the cell display element in the cell morphology image may be obtained, with respect to each of the plurality of cell display elements as all of the cell display elements in the virtual cell distribution image. Accordingly, in the setting unit 214 described below, a statistic of the characteristic value relevant to the characteristics in appearance of a plurality of assumed cell areas in the virtual cell distribution image can be calculated.

The setting unit 214 sets a value range which is used for correcting the virtual cell distribution image in the correction unit 215 described below. In the setting unit 214, at least one value range of a value range to be allowable (also referred to as an allowable value range) and a value range not to be allowable (also referred to as a prohibition value range) is set as the characteristic value relevant to one type or more characteristics in appearance, which is obtained in the arithmetic unit 213.

Here, the allowable value range with respect to each of one type or more characteristics may be a predetermined value range set in advance, or may be a value range set according to the characteristics of the virtual cell distribution image (also referred to as a variable value range). In addition, the prohibition value range with respect to each of one type or more characteristics may be the predetermined value range set in advance, or may be the variable value range set according to the characteristics of the virtual cell distribution image. That is, at least one of the allowable value range and the prohibition value range with respect to each of one type or more characteristics may be the predetermined value range set in advance, or may be the variable value range set according to the characteristics of the virtual cell distribution image. The variable value range, for example, can be set according to a rule set in advance from the statistic of the characteristic value relevant to each of one type or more characteristics with respect to the plurality of cell display elements in the virtual cell distribution image (also referred to as a setting rule). Accordingly, the variable value range according to the state of the assumed cell area in the cell morphology image can be set, and the virtual cell distribution image can be corrected by the correction unit 215 described below according to the state of the assumed cell area in the cell morphology image.

The statistic, for example, can be calculated as the statistic of the characteristic value with respect to the plurality of cell display elements, which is obtained by the arithmetic unit 213 with respect to each of the characteristics. For example, in a case where at least one value of an average value, a mode value, and a medium value is adopted as the statistic, it is possible to easily calculate the statistic, and it is possible to set a suitable variable value range. Furthermore, for example, an arithmetic average obtained by dividing the sum of the characteristic values with the sum total of the characteristic values can be adopted as the average value. The setting rule, for example, may be a rule for setting the variable value range by using the statistic as the criteria. In a case where the statistic is the statistic relevant to the size of the assumed cell area, for example, a rule for setting a value range of less than a predetermined ratio of the average value of the size as the prohibition value range as the variable value range, and/or a rule for setting a value range of greater than or equal to the predetermined ratio of the average value of the size as the allowable value range as the variable value range can be adopted. The predetermined ratio, for example, can be suitably set as 20% to 70%.

Figure 14:
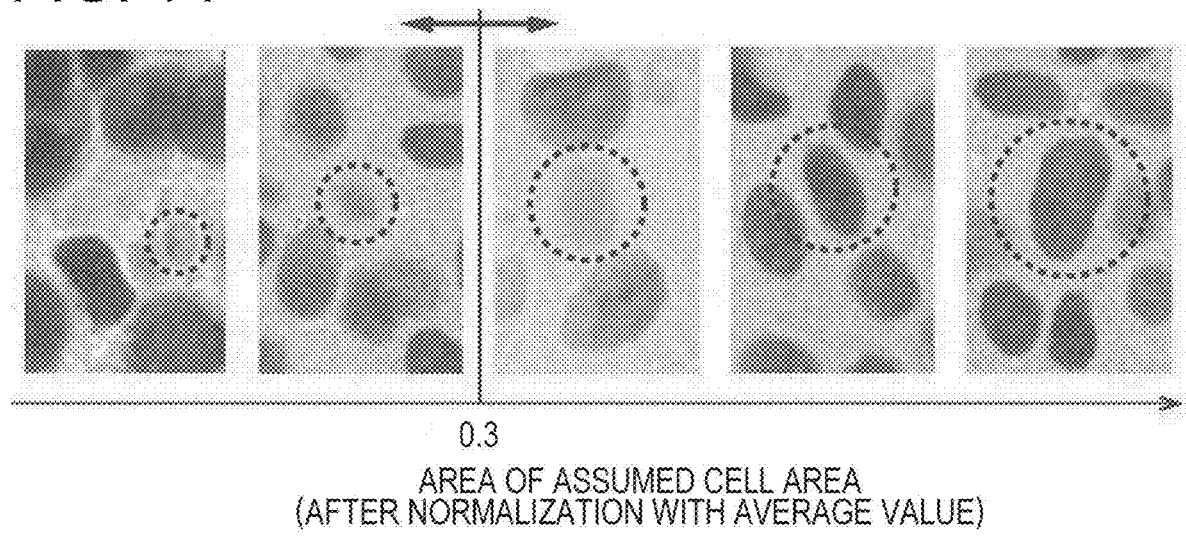
FIG. 14 is a diagram illustrating a setting example of a value range relevant to an area of the assumed cell area.
Figure 15:
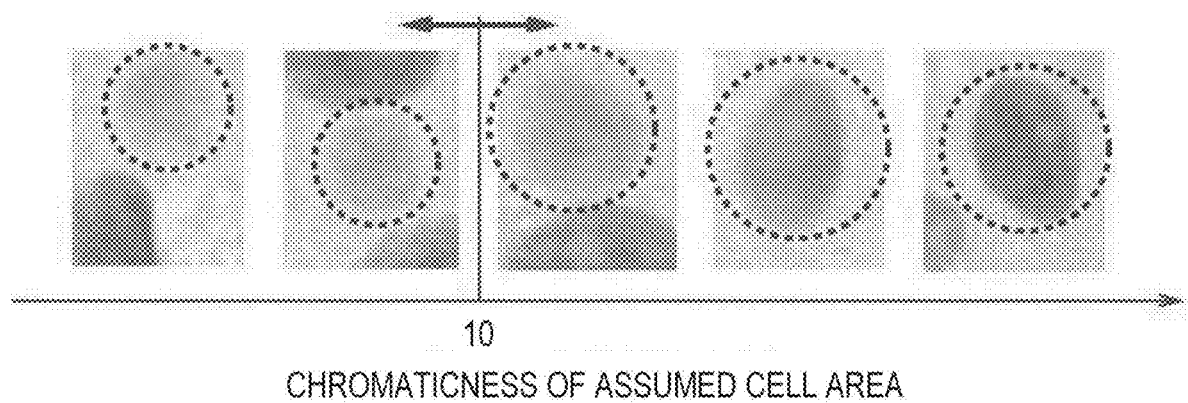
FIG. 15 is a diagram illustrating a setting example of a value range relevant to a chromaticness of the assumed cell area.
Figure 16:
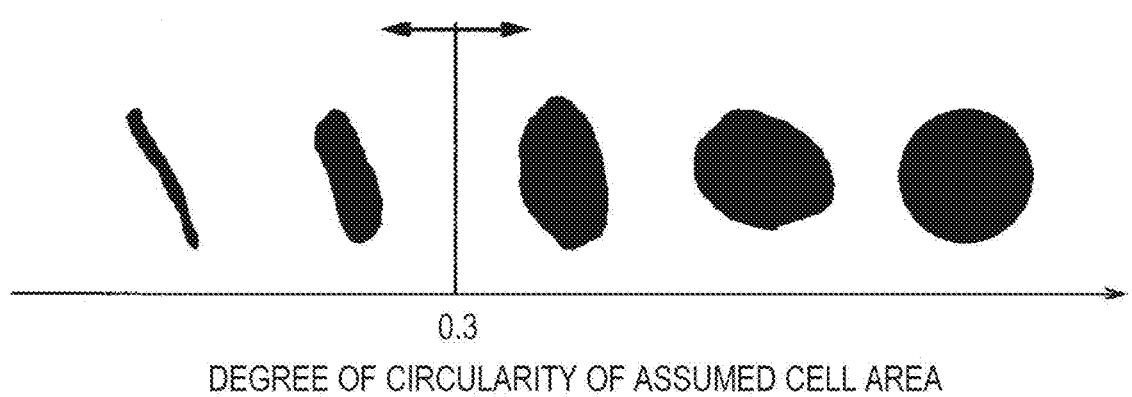
FIG. 16 is a diagram illustrating a setting example of a value range relevant to a degree of circularity of the assumed cell area.

FIGS. 14 to 16 are diagrams illustrating a setting example of the value range.

FIG. 14 illustrates an example in which an area, which is the characteristic value relevant to the size, is adopted as the characteristic value relevant to the characteristics in appearance of the assumed cell area. Specifically, a horizontal axis of FIG. 14 illustrates a value obtained after the area of the assumed cell area surrounded by a broken line in each of cell morphology images is divided by the arithmetic average of the areas of a plurality of assumed cell areas in the cell morphology image, and thus, is normalized (also referred to as an area after normalization). For this reason, FIG. 14 illustrates an aspect in which the area after normalization increases as being directed towards the right. Then, FIG. 14 illustrates an aspect in which 30% of the arithmetic average of the areas of the plurality of assumed cell areas (the average value) is set as a threshold value, a value range where the area after normalization is less than 0.3 is set as the prohibition value range, and a value range where the area after normalization is greater than or equal to 0.3 is set as the allowable value range.

FIG. 15 illustrates an example in which the chromaticness, which is the characteristic value relevant to the concentration, is adopted as the characteristic value relevant to the characteristics in appearance of the assumed cell area. Specifically, a horizontal axis of FIG. 15 illustrates the chromaticness of the assumed cell area surrounded by a broken line in each of the cell morphology images. For this reason, FIG. 15 illustrates an aspect in which the chromaticness increases as being directed towards the right. Then, FIG. 15 illustrates an aspect in which 10, which is a predetermined value set in advance with respect to the chromaticness, is set as the threshold value, a predetermined value range of less than the predetermined value is set as the prohibition value range, and a predetermined value range of greater than or equal to the predetermined value is set as the allowable value range.

FIG. 16 illustrates an example in which the degree of circularity, which is the characteristic value relevant to the shape, is adopted as the characteristic value relevant to the characteristics in appearance of the assumed cell area. Specifically, a horizontal axis of FIG. 16 illustrates the degree of circularity of each of the assumed cell areas. For this reason, FIG. 16 illustrates an aspect in which the degree of circularity increases as being directed towards the right. Then, FIG. 16 illustrates an aspect in which 0.3, which is a predetermined value set in advance with respect to the degree of circularity, is set as a threshold value, a predetermined value range of less than the predetermined value is set as the prohibition value range, and a predetermined value range of greater than or equal to the predetermined value is set as the allowable value range.

Figure 17:
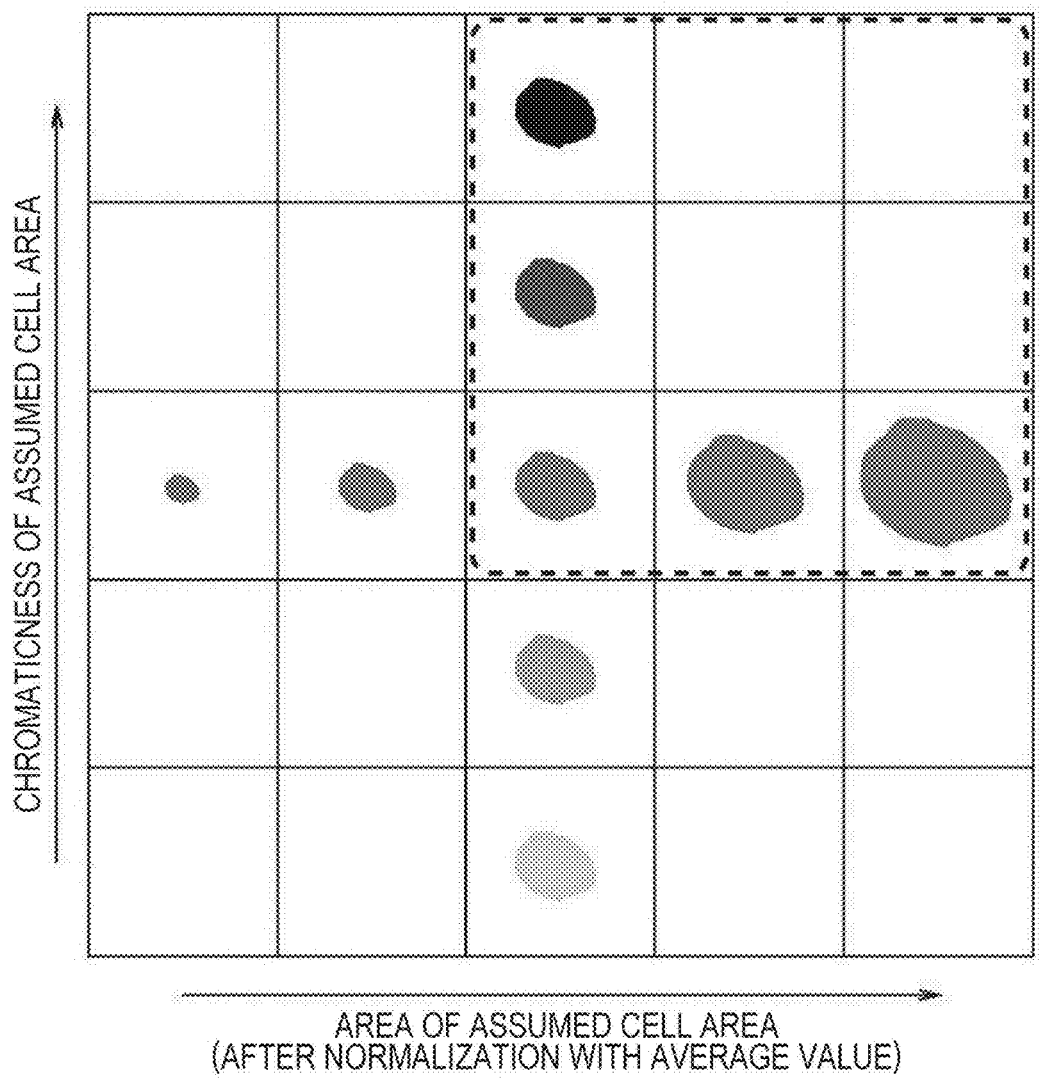
FIG. 17 is a diagram illustrating an example in which a value range of cutting processing is set with respect to two characteristics.

FIG. 17 illustrates an example in which the area, which is the characteristic value relevant to the size and the chromaticness, which is the characteristic value relevant to the concentration are adopted as the characteristic value relevant to characteristics in appearance of the assumed cell area. Here, an example is illustrated in which a two-dimensional value range is set in which the setting of the value range illustrated in FIG. 14 and the setting of the value range illustrated in FIG. 15 are combined with each other. Specifically, a horizontal axis of FIG. 17 illustrates a value obtained after the area of the assumed cell area is divided by the arithmetic average of the areas of the plurality of assumed cell areas in the cell morphology image (the average value), and thus, is normalized (also referred to as the area after normalization), and a vertical axis of FIG. 17 illustrates the chromaticness of the assumed cell area. Then, an aspect is illustrated in which the two-dimensional value range surrounded by a thick broken line is set as the allowable value range. At this time, a residual value range except for the two-dimensional value range surrounded by the thick broken line is set as the prohibition value range.

The correction unit 215 performs processing of deleting a cell display element of which the characteristic value obtained by the arithmetic unit 213 is at least out of the allowable value range or within the prohibition value range, in one or more cell display elements depicted in the virtual cell distribution image by the user, from the virtual cell distribution image (also referred to as cutting processing). Accordingly, the virtual cell distribution image is corrected, and the cell distribution image is generated. Thus, the virtual cell distribution image is corrected according to the value range which can be objectively set, and thus, for example, a variation rarely occurs in cell distribution images obtained between users. As a result thereof, the cell distribution image accurately representing the distribution of the cell area where the specific portion of the cell in the cell morphology image capturing the cell morphology is captured can be stably acquired. In particular, in a case where the variable value range is set according to the state of the assumed cell area in the cell morphology image, a more accurate cell distribution image can be acquired according to the cell morphology image.

Figure 18:
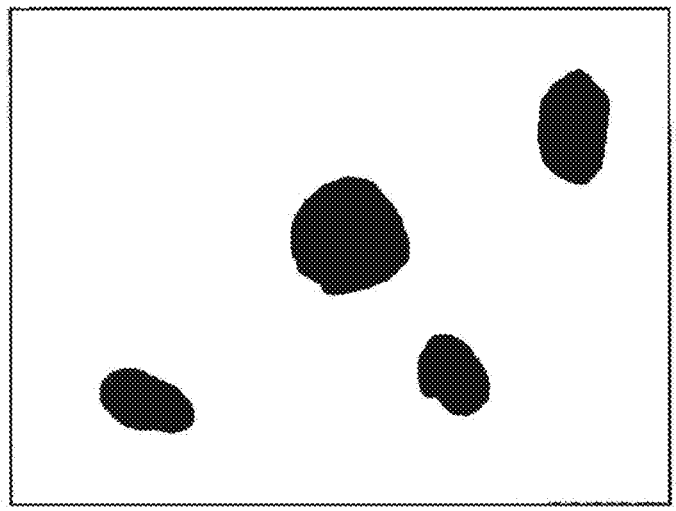
FIG. 18 is a diagram schematically illustrating an example of a cell distribution image which is generated by the cutting processing.

FIG. 18 is a diagram schematically illustrating an example of the cell distribution image which is generated by being corrected according to the cutting processing. FIG. 18 illustrates the cell distribution image which is generated by being corrected according to the cutting processing using the virtual cell distribution image illustrated in FIG. 13 as a target. Here, a cell distribution image generated by deleting an assumed cell area having at least one characteristic of a concentration of less than a certain degree, a size of less than a certain degree, and a flatness of greater than a certain degree is deleted is exemplified.

Figure 19:
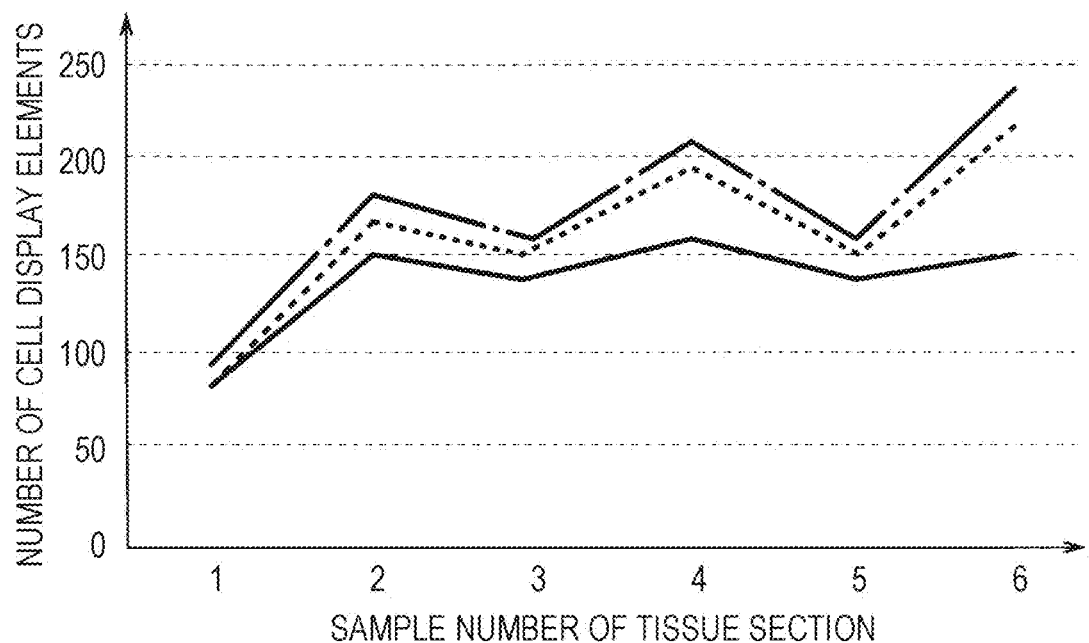
FIG. 19 is a diagram in which a variation in the number of cell display elements between operators in a case where the cutting processing is not performed is exemplified.
Figure 20:
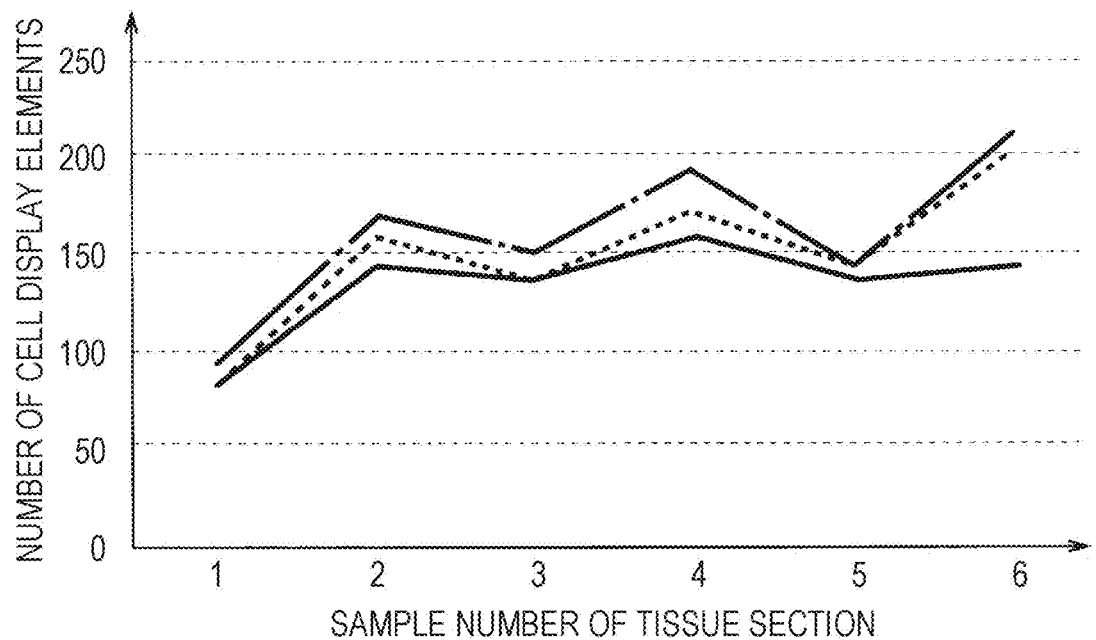
FIG. 20 is a diagram in which a variation in the number of cell display elements between the operators in a case where the cutting processing is performed is exemplified.

FIG. 19 and FIG. 20 are diagrams illustrating a specific example in which a variation occurring in cell distribution images to be obtained by different users is reduced by the cutting processing. Here, an example is illustrated in which cell distribution images with respect to six tissue sections (samples 1 to 6) are obtained by an operator A, an operator B, and an operator C as three users. In each of FIG. 19 and FIG. 20, the number of cell display elements existing in each of the cell distribution images relevant to six samples 1 to 6 generated by each of the operators A to C is illustrated by a polygonal line. Specifically, the number of cell display elements in the cell distribution image generated by the operator A each of the samples is illustrated by a polygonal line of a solid line. The number of cell display elements in the cell distribution image generated by the operator B with respect to each of the samples is illustrated by a polygonal line of a broken line. The number of cell display elements in the cell distribution image generated by the operator C with respect to each of the samples is illustrated by a polygonal line of a dot-and-dash line.

In FIG. 19, a variability between the operators with respect to the number of cell display elements existing in the cell distribution image which is generated without being subjected to the cutting processing, is exemplified. In FIG. 20, a variability between the operators with respect to the number of cell display elements existing in the cell distribution image which is generated by being subjected to the cutting processing, is exemplified. As illustrated in FIG. 19 and FIG. 20, a tendency is observed in which the variability between the operators with respect to the cell distribution images generated for each sample is reduced by performing the cutting processing. Specifically, an arithmetic average of variation coefficients (CV) relevant to a variation in the number of cell display elements occurring with respect to the same sample due to a difference in the operators, with respect to six samples, decreases from 11.6% to 9.4% by performing the cutting processing. That is, it is known that a variation in the cell distribution images between the operators can be reduced by performing the cutting processing.

The calculation unit 216 calculates the analysis value relevant to the existence state of the specific biological substance of the specific portion captured in the cell morphology image, on the basis of the cell distribution image generated by the correction unit 215, and the bright point distribution image obtained by the acquisition unit 211. Here, as the analysis value to be calculated, for example, a statistical value such as the number of fluorescent bright points per unit area (also referred to as the number of bright points) (that is, a statistic) can be adopted. For example, unit area of the cell area and one cell area can be adopted as the unit area. In this case, for example, the number of bright points per unit area, the number of bright points per one cell area, and the like can be calculated as the analysis value.

Figure 21:
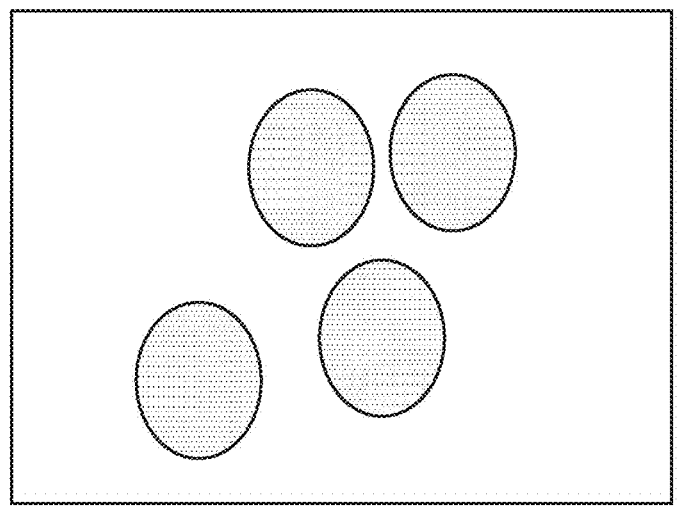
FIG. 21 is a diagram schematically illustrating an example of the cell distribution image.
Figure 22:
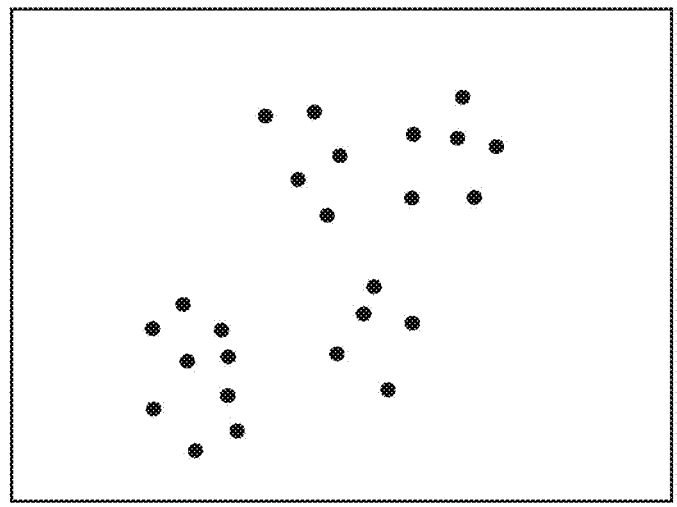
FIG. 22 is a diagram schematically illustrating an example of the bright point distribution image.
Figure 23:
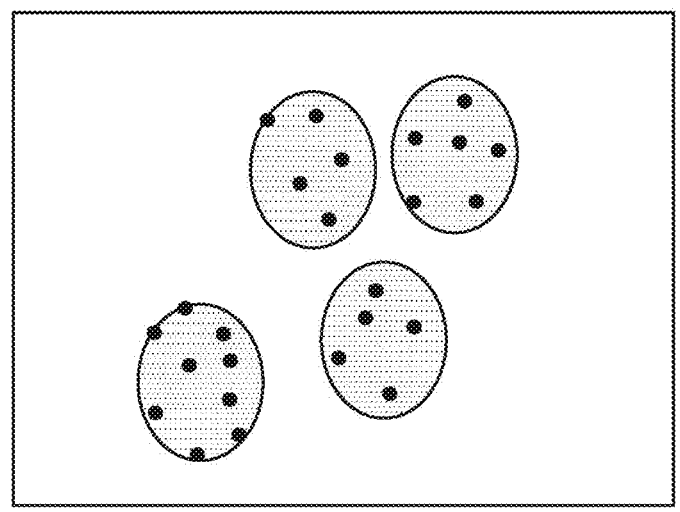
FIG. 23 is a diagram in which a relationship between the cell distribution image and the bright point distribution image is exemplified.

Here, for example, the cell distribution image as exemplified in FIG. 21 is superimposed on the bright point distribution image as exemplified in FIG. 22 as exemplified in FIG. 23, and thus, a relationship between the cell area and the fluorescent bright point can be recognized.

Figure 24:
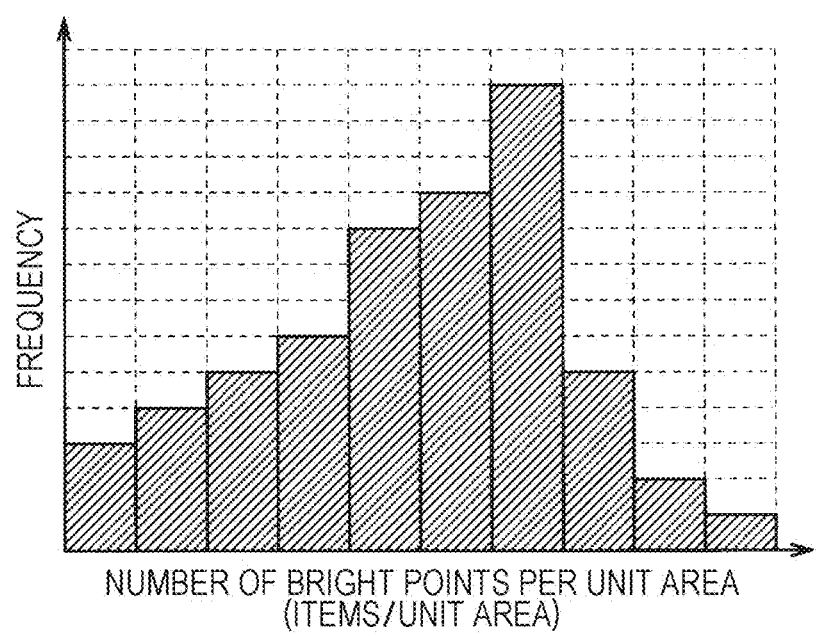
FIG. 24 is a graph in which a relationship between the number of bright points per unit area and a frequency thereof is exemplified.

FIG. 24 is a diagram illustrating an example of the analysis value relevant to the existence state of the specific biological substance with respect to the cell area. Specifically, a horizontal axis illustrates the number of bright points per unit area, and a vertical axis illustrates the number of occurrences of the number of bright points per unit area (a frequency). According to such statistical analysis data, it is possible to accurately perform a pathological diagnosis diagnosing the presence or absence, the type, or the like of a pathological change.

<(1-6) Operation Flow of Image Processing Device>

Figure 25:
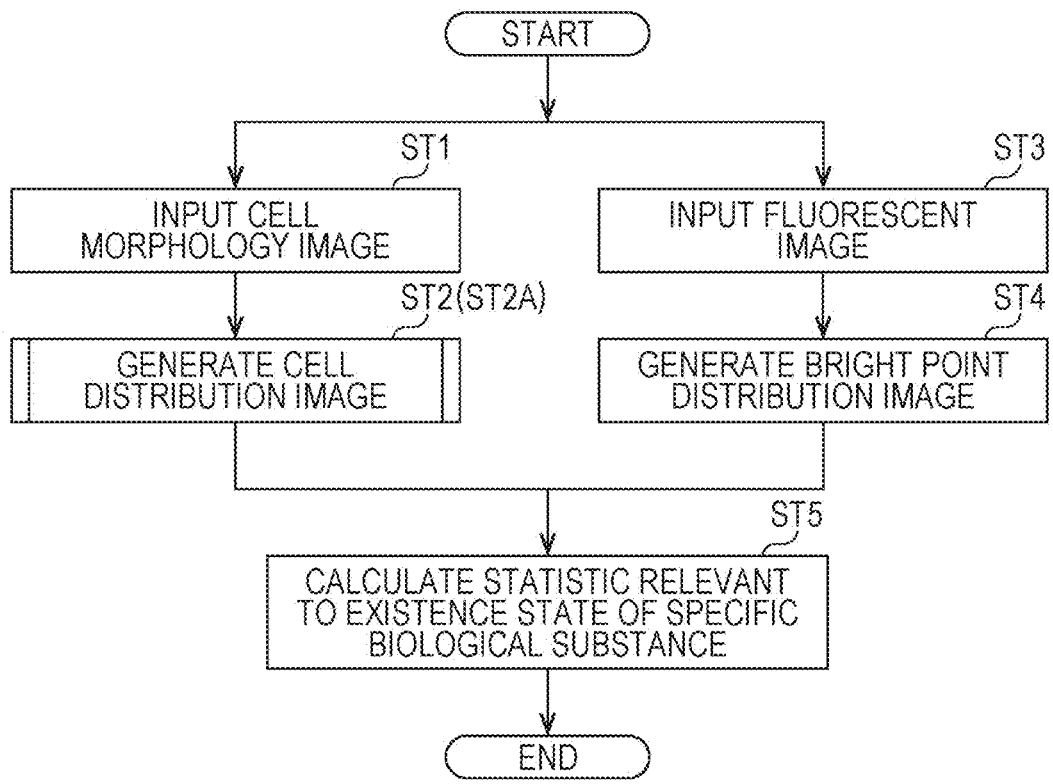
FIG. 25 is a diagram in which an operation flow of an image processing device is exemplified.
Figure 26:
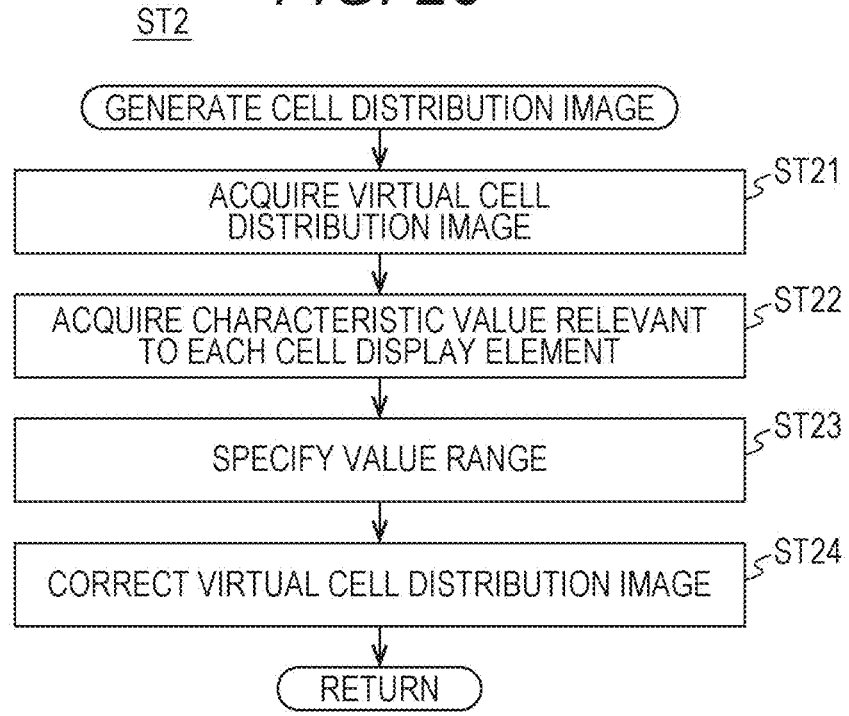
FIG. 26 is a diagram illustrating an example of an operation flow relevant to the generation of the cell distribution image.
Figure 27:
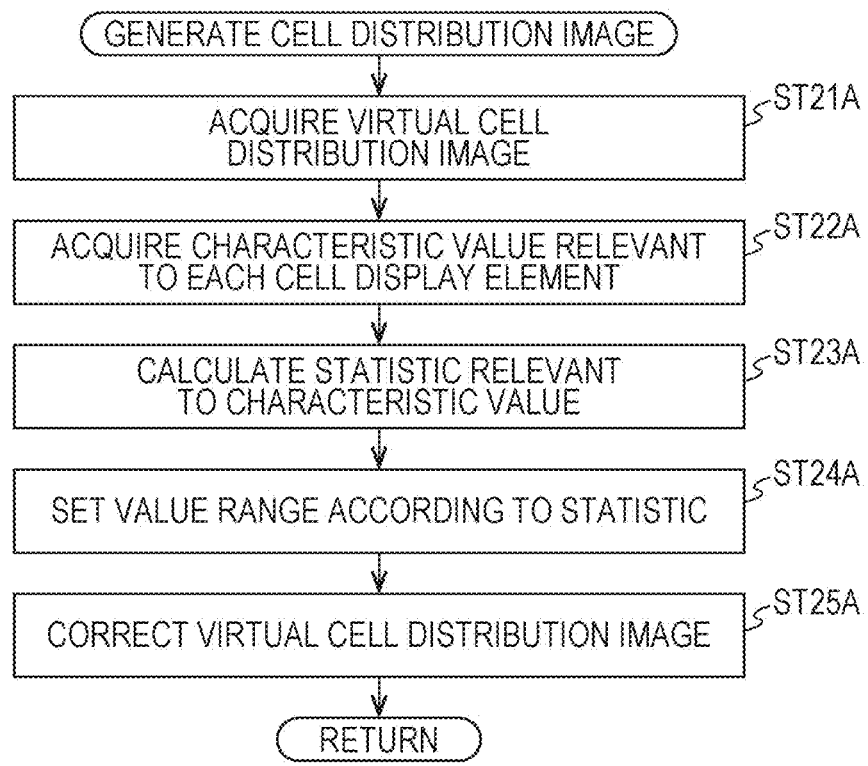
FIG. 27 is a diagram illustrating another example of the operation flow relevant to the generation of the cell distribution image.

FIGS. 25 to 27 are flowcharts in which an operation flow of the image processing device 2 is exemplified. Here, an example is illustrated in which the cell morphology image and the fluorescent image as the microscope image are input into the image processing device 2.

As illustrated in FIG. 25, in the image processing device 2, a series of processings in which processings of Steps ST1 and ST2 are sequentially performed, and the other series of processings in which processings of Steps ST3 and ST4 are sequentially performed are executed in parallel, and after that, processing of Step ST5 is performed. Furthermore, it is not necessary to execute the series of processings including Steps ST1 and ST2 and the series of processings including Steps ST3 and ST4 in parallel. For example, any one of the processing of Step ST1 and the processing of Step ST3 may be executed first. In addition, for example, in a case where the processing of Step ST2 is executed after the processing of Step ST1, the processing of Step ST2 may be executed at the same time as the processings of Steps ST3 and ST4, or may be executed at any timing before and after the processings of Steps ST3 and ST4. In addition, for example, in a case where the processing of Step ST4 is executed after the processing of Step ST3, the processing of Step ST4 may be executed at the same time as the processings of Steps ST1 and ST2, or may be executed at any timing before and after the processings of Steps ST1 and ST2.

In Step ST1, the cell morphology image is input into the control unit 21. Here, for example, the cell morphology image acquired by the microscope image acquisition device 1 is input into the control unit 21 through the communication I/F 24.

In Step ST2, the cell distribution image is generated by the acquisition unit 211 from the cell morphology image input in Step ST1. In Step ST2, for example, the operation flow illustrated in FIG. 26 is executed. Here, a series of processings is executed in which processings of Step ST21 to ST24 illustrated in FIG. 26 are sequentially performed.

In Step ST21 of FIG. 26, the virtual cell distribution image is acquired by the acquisition unit 211. As described above, the virtual cell distribution image is an image in which distribution of the assumed cell area to be assumed that the specific portion of the cell in the cell in the cell morphology image capturing the plurality of cell morphologies in the tissue section of the biological object stained with the predetermined staining reagent is captured is represented by the plurality of cell display elements. Then, in the virtual cell distribution image, one or more cell display elements are depicted according to the signal input according to the operation of the user in a state where the cell morphology image is displayed on the display unit 23, in the plurality of cell display elements. Furthermore, here, for example, the basic cell distribution image is obtained once by predetermined image processing using the cell morphology image input in Step ST1 as a target, and one or more cell display elements are added by the user with respect to the basic cell distribution image, and thus, the virtual cell distribution image is acquired.

In Step ST22, the characteristic value relevant to one type or more characteristics in appearance of the assumed cell area corresponding to the cell display element in the cell morphology image (the non-detection cell area) is acquired by the arithmetic unit 213, with respect to each of one or more cell display elements depicted by the user, in the virtual cell distribution image. Here, for example, the characteristic value relevant to at least one type of characteristics of the size, the denseness, and the shape of the assumed cell area is calculated.

In Step ST23, at least one value range of the allowable value range and the prohibition value range to be used in Step ST24 is set by the setting unit 214. Here, for example, at least one of the allowable value range and the prohibition value range is set to a predetermined value range set in advance.

In Step ST24, the cell display element of which the characteristic value acquired in Step ST22 is at least out of the allowable value range or within the prohibition value range is deleted from the virtual cell distribution image, in one or more cell display elements depicted according to the operation of the user, and thus, the virtual cell distribution image is corrected by the correction unit 215. Accordingly, the cell distribution image is generated.

Furthermore, a series of processings (Step ST2A) may be executed in which processings of Steps ST21A to ST25A illustrated in FIG. 27 are sequentially executed instead of executing Step ST2.

In Step ST21A of FIG. 27, processing similar to Step ST21 of FIG. 26 is performed.

In Step ST22A, the characteristic value relevant to one type or more characteristics in appearance of the assumed cell area corresponding to cell display element in the cell morphology image is acquired by the arithmetic unit 213, with respect to each of all of the plurality of cell display elements including one or more cell display elements depicted by the user, in the virtual cell distribution image.

In Step ST23A, the statistic of the characteristic values with respect to the plurality of cell display elements obtained in Step ST22A is calculated by the arithmetic unit 213, with respect to each of the characteristics.

In Step ST24A, at least one variable value range of the allowable value range and the prohibition value range, used in Step ST25A, is set by the setting unit 214, according to the setting rule set in advance from the statistic relevant to the characteristic value calculated in Step ST23A, with respect to each of the characteristics.

In Step ST25A, the cell display element of which the characteristic value acquired in Step ST22A is out of the allowable value range or within the prohibition value range, set in Step ST24A, is deleted from the virtual cell distribution image by the correction unit 215, in one or more cell display elements depicted according to the operation of the user, and thus, the virtual cell distribution image is corrected. Accordingly, the cell distribution image is generated.

Thus, in Steps ST2 and ST2A, the cell display element is deleted according to the predetermined value range or the variation value range, but the present invention is not limited thereto. For example, in a case where the cell display element is deleted according to at least one value range of the allowable value range and the prohibition value range of two types or more characteristics, the processings included in Steps ST2 and ST2A may be suitably combined within a range which is not contradictory.

Returning to FIG. 25, in Step ST3, the fluorescent image is input into the control unit 21. Here, the fluorescent image acquired by the microscope image acquisition device 1 is input into the control unit 21 through the communication I/F 24.

In Step ST4, the bright point distribution image is generated by the acquisition unit 211 from the fluorescent image input in Step ST3. Here, as described above, for example, the image processing is performed with respect to the fluorescent image, and thus, the bright point distribution image is generated.

In Step ST5, the analysis value relevant to the existence state of the specific biological substance with respect to the cell area is calculated by the calculation unit 216, on the basis of the cell distribution image generated in Step ST2 and the bright point distribution image generated in Step ST4.

<(1-7) Summary>

As described above, according to the image processing device relevant to this embodiment, the cell display element depicted by the user is deleted according to the characteristics in appearance of the assumed cell area relevant to the cell display element, and thus, the virtual cell distribution image is corrected, and the cell distribution image is generated. For this reason, for example, a variation rarely occurs in the cell distribution image obtained between the users. As a result thereof, it is possible to stably acquire the cell distribution image accurately representing the distribution of the area where the specific portion of the cell is captured in the image capturing the cell morphology. In particular, in a case where the variable value range is set according to the state of the assumed cell area in the cell morphology image, it is possible to acquire a more accurate cell distribution image according to the cell morphology image. Then, a variation rarely occurs in the cell distribution image obtained between the users, and thus, a variation rarely occurs even in the analysis value relevant to the existence state of the specific biological substance with respect to the specific portion, which is obtained from the cell distribution image and the bright point distribution image. As a result thereof, it is possible to improve the accuracy of the pathological diagnosis through the analysis of the microscope image.

(2) Modification Example

Furthermore, the present invention is not limited to one embodiment described above, and various changes, modifications, and the like can be performed within a range not departing from the gist of the present invention.

For example, in one embodiment described above, an aspect has been adopted in which only one or more cell display elements can be a correction target in the plurality of cell display elements of the virtual cell distribution image, but the present invention is not limited thereto. For example, an aspect may be adopted in which a part of the cell display element other than one or more cell display elements can also be the correction target in the plurality of cell display elements of the virtual cell distribution image, and an aspect may be adopted in which all of the cell display elements can be the correction target. That is, for example, an aspect may be adopted in which at least one or more cell display elements in the virtual cell distribution area can be the correction target.

In addition, in one embodiment described above, the characteristic value relevant to one type or more characteristics in appearance of the assumed cell area corresponding to the cell display element of the cell morphology image can be obtained by the arithmetic unit 213, with respect to each of one or more cell display elements depicted by the user, in the virtual cell distribution image, but the present invention is not limited thereto. For example, by the arithmetic unit 213, the characteristic value relevant to one type or more characteristics in appearance may be obtained with respect to each of one or more cell display elements depicted by the user, in the virtual cell distribution image. In addition, for example, the characteristic value relevant to one type or more characteristics in appearance may be obtained with respect to each of the plurality of cell display elements in the virtual cell distribution image. That is, the characteristic value relevant to the characteristics in appearance of the cell display element itself may be obtained.

That is, the characteristic value relevant to at least one type of characteristics of one type or more characteristics in appearance and one type or more characteristics in appearance of the assumed cell area corresponding to the cell display element in the cell morphology image may be obtained by the arithmetic unit 213, with respect to each of one or more cell display elements depicted by the user, in the virtual cell distribution image. In addition, for example, the characteristic value relevant to at least one type of characteristics of one type or more characteristics in appearance and one type or more characteristics in appearance of the assumed cell area corresponding to the cell display element in the cell morphology image may be obtained with respect to each of the plurality of cell display elements in the virtual cell distribution image.

In such a configuration, the cell display element depicted by the user is suitably deleted according to at least one characteristic in appearance of the cell display element and the assumed cell area in the cell morphology image corresponding to the cell display element, and thus, the virtual cell distribution image can be corrected, and the cell distribution image can be generated. Accordingly, for example, a variation rarely occurs in the cell distribution image obtained between the users. As a result thereof, it is possible to stably acquire the cell distribution image accurately representing the distribution of the cell area where the specific portion of the cell in the cell morphology image capturing the cell morphology is captured.

In addition, in a case where such a configuration is adopted, one type or more characteristics in appearance, for example, are capable of including at least one characteristic of the size, the denseness, and the shape with respect to the cell display element. Specifically, the characteristics relevant to the size, for example, are capable of including one type or more characteristics of a plurality of types of characteristics such as the area of the cell display element, the circumferential length, the length of the long axis, and the length of the short axis. In addition, in a case where the denseness of the cell display element corresponds to the denseness of the corresponding assumed cell area (for example, the arithmetic average of the denseness), the characteristics relevant to the denseness, for example, are capable of including one type or more characteristics of a plurality of types of characteristics such as the color phase, the luminosity, the chromaticness, and the color difference of the cell display element. In addition, the characteristics relevant to the shape, for example, are capable of including one type or more characteristics of a plurality of types of characteristics such as the degree of circularity, the flatness ratio, and the aspect ratio of the cell display element.

That is, one type or more characteristics in appearance, for example, are capable of including at least one characteristic of the size, the denseness, and the shape with respect to at least one of the assumed cell area and the cell display element. Specifically, the characteristics relevant to the size, for example, are capable of including one type or more characteristics of the plurality of types of characteristics such as the area, the circumferential length, the length of the long axis, and the length of the short axis, with respect to at least one of the assumed cell area and the cell display element. In addition, the characteristics relevant to the denseness, for example, are capable of including one type or more characteristics of the plurality of types of characteristics such as the color phase, the luminosity, the chromaticness, and the color difference, with respect to at least one of the assumed cell area and the cell display element. In addition, the characteristics relevant to the shape, for example, are capable of including one type or more characteristics of the plurality of types of characteristics such as the degree of circularity, the flatness ratio, and the aspect ratio, with respect to at least one of the assumed cell area and the cell display element.

Further, in a case where such a configuration is adopted, the statistic of the characteristic value with respect to at least one characteristic in appearance of the cell display element and the assumed cell area in the cell morphology image corresponding to the cell display element can be calculated by the arithmetic unit 213. Then, at least one variable value range of the allowable value range and the prohibition value range, used in the correction unit 215 can be set by the setting unit 214, according to the setting rule set in advance from the statistic relevant to the characteristic value calculated by the arithmetic unit 213, with respect to each of the characteristics.

In addition, in one embodiment described above, by the setting unit 214, the predetermined value range, or the variation value range according to the statistic relevant to the characteristic value is set as the allowable value range and the prohibition value range, but the present invention is not limited thereto. For example, at least one of the allowable value range or the prohibition value range, and at least one type of characteristics where the characteristic value is obtained may be set by the setting unit 214, according to the type of cell morphology image. Accordingly, the cell area, which is an analysis target, can be accurately extracted according to the characteristics of the cell morphology image. In other words, the value range, the characteristics, a combination of the characteristics, and the like are suitably set according to the state of the assumed cell area in the cell morphology image, and thus, the cell distribution image can be accurately acquired. As a result thereof, the analysis value relevant to the existence state of the specific biological substance with respect to the cell area can be more stably and accurately calculated.

Here, the type of cell morphology image, for example, is capable of including a cell morphology image imaging a tissue section isolated by a surgery (also referred to as a surgery specimen) as a target (also referred to as a surgery specimen image), a cell morphology imaging a tissue section obtained by a needle biopsy as a target (also referred to as a needle biopsy image), and the like. Here, identification information representing the type of cell morphology image is described in tag information of the cell morphology image, and the type of cell morphology image can be easily identified with reference to the tag information in the setting unit 214. Then, in a needle biopsy, when the tissue section is sampled, there is a case where a compression force is applied to a cell, and the shape of the cell is distorted. For this reason, an aspect is considered in which the allowable value range relevant to the size and the shape is set to be relatively wider, and the prohibition value range is set to be relatively narrower, in a case where the cell morphology image is a needle biopsy image than a case where the cell morphology image is a surgery specimen image. In addition, for example, the allowable value range or the prohibition value range may be set with respect to other characteristics such as the denseness, except for the characteristics such as the size and the shape.

Figure 28:
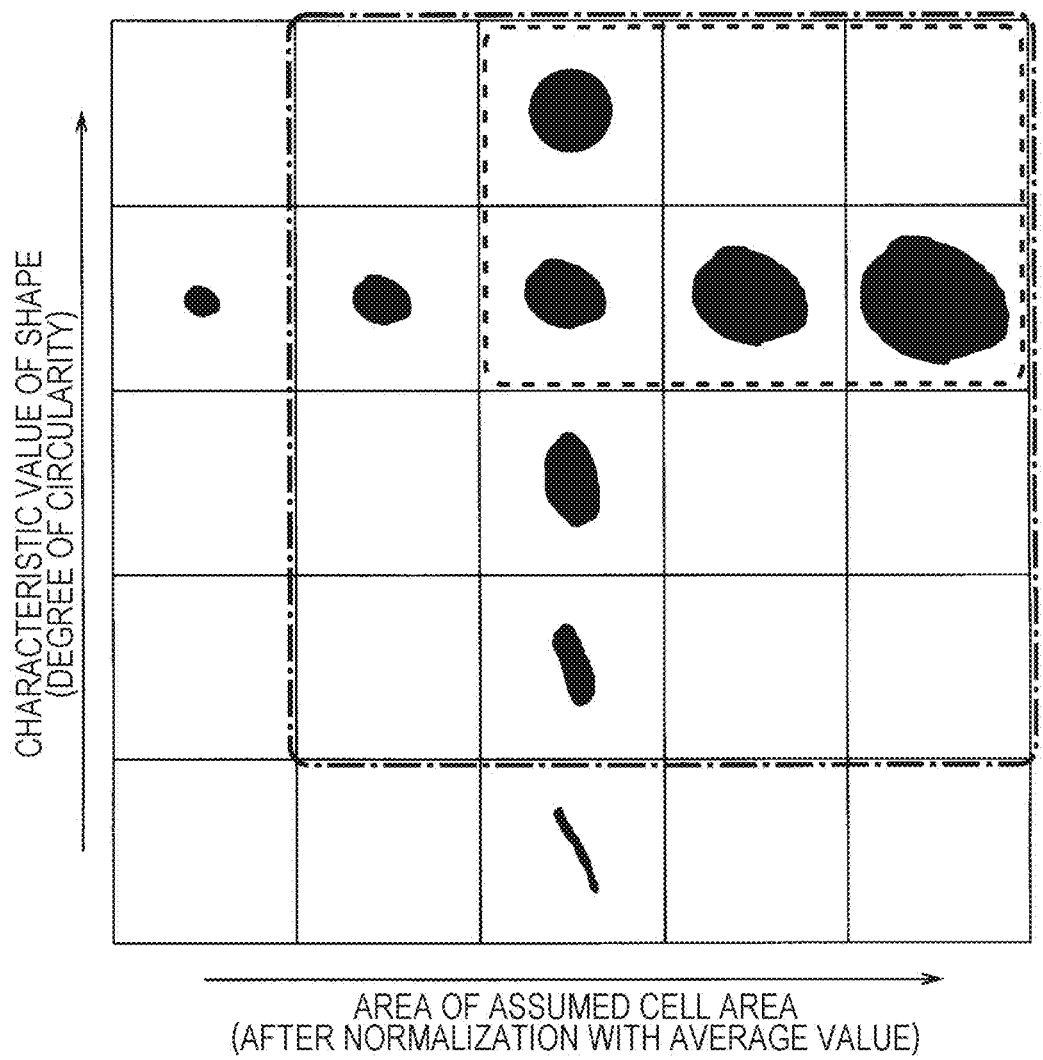
FIG. 28 is a diagram illustrating an example in which a value range is changed according to the type of cell morphology image.

FIG. 28 is a diagram illustrating an example in which the value range is changed according to the type of cell morphology image. FIG. 28 illustrates an example in which the area, which is the characteristic value relevant to the size, and the degree of circularity, which is the characteristic value relevant to the shape, are adopted as the characteristic value relevant to the characteristics in appearance of the assumed cell area. Here, a horizontal axis of FIG. 28 illustrates a value obtained after the area of the assumed cell area is divided by the arithmetic average (the average value) of the areas of the plurality of assumed cell areas in the cell morphology image, and thus, is normalized (also referred to as an area after normalization), and a vertical axis of FIG. 28 illustrates the degree of circularity of the assumed cell area. Then, for example, in a case where the cell morphology image is the surgery specimen image, a comparatively narrow two-dimensional value range surrounded by a thick broken line is set as the allowable value range, and in a case where the cell morphology image is the needle biopsy image, a comparatively wide two-dimensional value range surrounded by a thick dot-and-dash line is set as the allowable value range. Furthermore, at this time, the residual value range except for the two-dimensional value range surrounded by the thick broken line is set as the prohibition value range with respect to the surgery specimen image, and the residual value range except for the two-dimensional value range surrounded by the thick dot-and-dash line is set as the prohibition value range with respect to the needle biopsy image.

In addition, in one embodiment described above, in the correction unit 215, the cell display element of which the characteristic value obtained by the arithmetic unit 213 is out of the allowable value range or within the prohibition value range, is deleted from the virtual cell distribution image, in one or more cell display elements of the virtual cell distribution image, depicted by the user, but the present invention is not limited thereto. For example, in the correction unit 215, the cell display element of which the characteristic value obtained by the arithmetic unit 213 is out of the allowable value range or within the prohibition value range, may be set to be in an unadopted state, in one or more cell display elements of the virtual cell distribution image, depicted by the user, and thus, the virtual cell distribution image may be corrected. Here, for example, a state which is not adopted in the analysis processing can be adopted as the unadopted state. Furthermore, an aspect or the like is considered in which information representing that the cell display element is set to be in the unadopted state suitably includes the tag information of the cell distribution image along with positional information specifying the cell display element which is not adopted.

In addition, in one embodiment described above, in the acquisition unit 211, the basic cell distribution image is obtained once by the predetermined image processing using the cell morphology image as the target, and one or more cell display elements are added by the user with respect to the basic cell distribution image, and thus, the virtual cell distribution image is acquired, but the present invention is not limited thereto. For example, in the acquisition unit 211, all of the cell display elements may be depicted according to the operation of the user without performing the predetermined image processing using the cell morphology image as the target, and thus, the virtual cell distribution image may be acquired.

In addition, in one embodiment described above, in the image processing device 2, the cell morphology image and the fluorescent image are obtained from the microscope image acquisition device 1, but the present invention is not limited thereto. For example, in the image processing device 2, at least one image of the basic cell distribution image and the bright point distribution image may be obtained from the external device or the storage medium.

In addition, in one embodiment described above, one information processing device functions as the image processing device 2 executing various processings, but the present invention is not limited thereto. For example, the various processings may be executed in an information processing system formed of a plurality of information processing devices, or may be executed in an information processing system in various aspects such as an application service provider (ASP) and cloud computing. That is, the image processing device 2 is not limited to be configured of a single information processing device, and may have an aspect of a system performing image processing realized by the cooperation of a plurality of information processing devices (also referred to as an image processing system).

Furthermore, it is obvious that all or a part configuring each of one embodiment described above and various modification examples can be suitably combined within a range which is not contradictory.

REFERENCE SIGNS LIST

1 microscope image acquisition device
2 image processing device
21 control unit
22 input unit
23 display unit
25 storage unit
100 pathological diagnosis support system
211 acquisition unit
212 display control unit
213 arithmetic unit
214 setting unit
215 correction unit
216 calculation unit
P1 program

The invention claimed is:

1. An image processing device, comprising:
a display control unit that displays a cell morphology image capturing a cell morphology in a tissue section of a biological object stained with a staining reagent on a display unit;
an input unit that inputs a signal according to an operation of a user;
an acquisition unit that acquires a virtual cell distribution image from the cell morphology image, the virtual cell distribution image depicting one or more cell display elements of a plurality of cell display elements, according to the signal from the input unit, and representing a specific portion of a cell in the cell morphology image by the one or more cell display elements, and the cell morphology image is displayed on the display unit;
an arithmetic unit that obtains a characteristic value relevant to at least one type of appearance characteristic of the specific portion of the cell, wherein at least one type of appearance characteristic corresponds to the cell display element of the cell morphology image; and
a correction unit that corrects the virtual cell distribution image to generate a cell distribution image by setting a cell display element of which the characteristic value is at least out of an allowable value range or within a prohibition value range to be in a state of being deleted from the virtual cell distribution image or being unadopted, in the one or more cell display elements.

2. The image processing device according to claim 1, wherein at least one value range of the allowable value range and the prohibition value range with respect to the characteristic value relevant to each of the at least one type of characteristics includes a predetermined value range set in advance, or a variable value range set according to a rule set in advance from a statistic relevant to the characteristic value of each of the at least one type of characteristics with respect to the plurality of cell display elements.

3. The image processing device according to claim 2, wherein the statistic includes at least one value of an average value, a mode value, and a medium value.

4. The image processing device according to claim 1, wherein the one type or more characteristics in appearance include at least one characteristic of a size, a denseness, and a shape.

5. The image processing device according to claim 4, wherein a characteristic relevant to the size includes one type or more characteristics of an area, a circumferential length, a length of a long axis, and a length of a short axis, with respect to at least one of the cell display element and the specific portion of the cell,
a characteristic relevant to the denseness includes one type or more characteristics of a color phase, a luminosity, a chromaticness, a brightness, and a color difference, with respect to at least one of the cell display element and the specific portion of the cell, and
a characteristic relevant to the shape includes one type or more characteristics of a degree of circularity, a flatness ratio, and an aspect ratio, with respect to at least one of the cell display element and the specific portion of the cell.

6. The image processing device according to claim 1, further comprising:
a setting unit that sets at least one of the allowable value range or the prohibition value range, and the at least one type of characteristics, according to the type of cell morphology image.

7. The image processing device according to claim 1, wherein the acquisition unit acquires a bright point distribution image representing a distribution of a fluorescent bright point relevant to a specific wavelength of a fluorescent image capturing the tissue section in which a specific biological substance is stained with a fluorescent staining reagent, and
the image processing device further includes a calculation unit that calculates an analysis value relevant to an existence state of the specific biological substance in the specific portion captured in the cell morphology image, on the basis of the cell distribution image and the bright point distribution image.

8. An image processing method, comprising:
(a) a step of acquiring a virtual cell distribution image depicting one or more cell display elements of a plurality of cell display elements, according to a signal input according to an operation of a user, wherein the virtual cell distribution image represents a specific portion of a cell in a cell morphology image capturing a cell morphology in a tissue section of a biological object stained with a staining reagent, the specific portion of the cell is represented by the one or more cell display elements, and the cell morphology image is displayed on a display unit, by an acquisition unit;

(b) a step of obtaining a characteristic value relevant to at least one type of appearance characteristic of the specific portion of the cell, wherein at least one type of appearance characteristic corresponds to the cell display element of the cell morphology image, in each of the one or more cell display elements, by an arithmetic unit; and (c) a step of correcting the virtual cell distribution image to generate a cell distribution image by setting a cell display element of which the characteristic value is at least out of an allowable value range or within a prohibition value range to be in a state of being deleted from the virtual cell distribution image or being unadopted, in the one or more cell display elements, by a correction unit.

9. A computing system comprising
a processor; and
a memory comprising instructions, that when executed on the processor, cause the computing system to at least:

(a) acquire a virtual cell distribution image depicting one or more cell display elements of a plurality of cell display elements, according to a signal input according to an operation of a user, wherein the virtual cell distribution image represents a specific portion of a cell in a cell morphology image capturing a cell morphology in a tissue section of a biological object stained with a staining reagent, the specific portion of the cell is represented by the one or more cell display elements, and the cell morphology image is displayed on a display unit, by an acquisition unit;

(b) obtain a characteristic value relevant to at least one type of appearance characteristic of the specific portion of the cell, wherein at least one type of appearance characteristic corresponds to the cell display element of the cell morphology image, in each of the one or more cell display elements, by an arithmetic unit, and (c) correct the virtual cell distribution image to generate a cell distribution image by setting a cell display element of which the characteristic value is at least out of an allowable value range or within a prohibition value range to be in a state of being deleted from the virtual cell distribution image or being unadopted, in the one or more cell display elements, by a correction unit.

* * * * *